(12) United States Patent
Han et al.

(10) Patent No.: US 8,329,115 B2
(45) Date of Patent: Dec. 11, 2012

(54) NANOFLUIDIC PRECONCENTRATION DEVICE IN AN OPEN ENVIRONMENT

(75) Inventors: Jongyoon Han, Bedford, MA (US); Sung Jae Kim, Melrose, MA (US); Dustin Moon, Malden, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 489 days.

(21) Appl. No.: 12/624,378

(22) Filed: Nov. 23, 2009

(65) Prior Publication Data

US 2010/0187112 A1  Jul. 29, 2010

Related U.S. Application Data

(60) Provisional application No. 61/117,506, filed on Nov. 24, 2008.

(51) Int. Cl.
*G01N 27/447* (2006.01)
*G01N 27/453* (2006.01)

(52) U.S. Cl. ......... 422/502; 204/451; 204/601; 137/833
(58) Field of Classification Search .......... 204/450–454, 204/600–604; 137/833; 422/502–508
See application file for complete search history.

(56) References Cited

U.S. PATENT DOCUMENTS

2006/0060769 A1 * 3/2006 Bousse et al. ................. 250/282

* cited by examiner

*Primary Examiner* — J. Christopher Ball
(74) *Attorney, Agent, or Firm* — Gesmer Updegrove LLP

(57) ABSTRACT

This invention provides a device and methods for increasing the concentration of a charged species in solution, wherein the solution containing the concentrated species is exposed to the environment. Such solution can be formed on a surface or on a tip of a measurement device. The open-environment concentration technique overcomes the disadvantages of in-channel concentration devices, especially by eliminating flow-induced delivery processes that lead to concentration losses. Combined with direct contact dispensing, methods of this invention can be used for various applications such as immunoassay and MALDI-MS.

45 Claims, 3 Drawing Sheets

(a)

(b)

NANOFLUIDIC PRECONCENTRATION DEVICE IN AN OPEN ENVIRONMENT

CROSS REFERENCE TO RELATED APPLICATIONS

This Application claims the benefit of U.S. Provisional Application Ser. No. 61/117,506, filed Nov. 24, 2008, which is hereby incorporated by reference in its entirety.

GOVERNMENT INTEREST STATEMENT

This invention was made with government support under Grant Nos. CA119402 and EB005743 awarded by the National Institutes of Health. The government has certain rights in this invention.

BACKGROUND OF THE INVENTION

Due to the low abundance of most information-rich bio/chemical species to be detected, the amplification/preconcentration of such species has become the most important issues in bioanalytical research and industry. Considerable improvement in the non-genomic preconcentration methods have been achieved in the last decade, leading at least 100-1000 fold accumulation in sensitivity. Available methods include physical filtration and various novel approaches were studied such as field-amplified sample stacking (PASS), field-amplified sample injection (FASI), isotachophoretic stacking (ITP) and liquid-liquid extraction (LLE). Million-fold amplification of peptides and proteins using micro- and nano-channel hybridized system has been reported. Such methods utilized novel concentration polarization (CP) phenomena near nanochannels where the sample can stay and be accumulated at the ion depletion boundary which was created by CP. However, micro/nanochannels are usually fabricated within the material boundaries confining the flow of the sample. Due to the extremely high concentration gradient after preconcentration procedure, diffusion and dispersion inside the microchannel are critical, limiting the delivery of such high concentrated sample to a desired location such as mass spectrometry (MS) and matrix-assisted laser desorption/ionization-MS (MALDI-MS) systems. In this manner, dispersionless extraction of the concentrated plug has been an important issue. Electrodiffusion, which is proportional to the concentration gradient, or dispersion, which is proportional to the length it travels through, can be controlled only by having less travel length and time from the point of concentration to the point of detection. In this manner, many researchers tried detecting samples inside the channel rather than taking it out, but this limits the usage of the concentration device.

Many efforts have been made for carrying immunoassay inside microchannels in order to utilize the electrokinetic trapping preconcentration. However, implementing immunoassay within a microchannel is generally challenging, especially due to issues related to surface chemistry to immobilize antibodies and other chemical reagents required for immunoassays. On the other hand, conventional immunoassay processes (such as ELISA) were done on open surfaces, with much more robust control on surface chemistry and easier detection. To enjoy both advantages of conventional open surface immunoassays and efficient sample concentration by nanofluidic preconcentration, a preconcentration process outside the microchannel is highly desired.

SUMMARY OF THE INVENTION

In one embodiment, this invention provides a new method of concentrating low-abundance molecular species using the CP-enabled preconcentration process, but within a droplet on a surface. By having a droplet in between an inlet microchannel and an outlet microchannel, the droplet itself acts as a droplet chamber to concentrate low-abundance species. In one embodiment, this invention demonstrates an electrokinetic preconcentration process inside the droplet using fluorescence dye, thus successfully proving the concept of such device. After preconcentration, the accumulated molecules can be detected using conventional immunoassays and other techniques (MALDI-MS or ELISA), without the need for integrating the detectors to the microfluidic system directly.

In one embodiment, this invention provides an electrokinetic concentration device comprising:
  at least one concentration unit positioned such that at least a portion of the concentration unit is constructed within, adhered to or contiguous with a first substrate, the concentration unit comprising:
    at least one first sample microchannel through which a liquid comprising charged species can be made to pass from a first side to a second side, wherein at least a portion of the first channel is exposed to the environment;
    at least one second sample microchannel through which the liquid comprising charged species can be made to pass from a first side to a second side, wherein at least a portion of the second channel is exposed to the environment;
    at least one buffer microchannel or reservoir comprising a buffer;
    at least one conduit proximal to the sample microchannels and linked to the buffer microchannel or reservoir; and
    at least one unit to induce an electric field in the conduit, the sample microchannel, the buffer microchannel or reservoir or a combination thereof.

In one embodiment, the sample microchannels comprise liquid or solution comprising a charged species of interest and wherein the concentration unit comprises a droplet of the liquid or solution, the droplet at least partially exposed to the environment, wherein the droplet is in contact with the sample microchannels and the conduit.

In one embodiment, at least a portion of the concentration unit is positioned proximally to or adhered to a plate, wherein the plate supports, seals and/or stabilizes at least a portion of the concentration unit.

In one embodiment, the plate is in contact with the droplet.

In one embodiment, the conduit comprising a polymer-based permselective material comprising a cation selective or an anion selective material.

In one embodiment, the device is comprised of a transparent material wherein the transparent material is pyrex, silicon dioxide, polydimethylsiloxane (PDMS), silicon nitride, quartz or SU-8.

In one embodiment, the concentration device comprising an array of concentration units.

In one embodiment, the concentration units within an array are stacked such that the two long axes of each unit are arranged in parallel to the two long axes of a neighboring concentration unit, and such that the region of the microchannels that is exposed to the environment in at least two of the units is directed to the same side with respect to the at least two concentration units.

In one embodiment, the concentration units within an array are positioned such that the shortest axis and one of the longer axes of the units are arranged in parallel to the shortest axis and one of the longer axes of a neighboring concentration unit, and such that the region of the microchannels that is exposed to the environment in at least two of the units is directed to the same side with respect to the at least two concentration units.

In one embodiment, the droplets are on the same plane.

In one embodiment, the array is positioned on top of a substrate.

In one embodiment, the array is fixed to the substrate.

In one embodiment, the regions on the substrate that are proximal to the droplets are coated with an indicator species, capable of interacting with the charged species.

In one embodiment, the regions on the substrate that are proximal to the droplet are connected to a measurement device, wherein the measurement device optionally measures fluorescence.

In one embodiment, the regions on the substrate that are proximal to the droplets fit a syringe or a dispenser array.

In one embodiment, the syringe or dispenser array is used to transfer the contents of the regions on the substrate which are proximal to the droplets to an assay system.

In one embodiment, the syringe or dispenser array is used to add assay material to the regions on the substrate that are proximal to the droplets.

In one embodiment, the spacing between rows or columns or combination thereof within the array approximates in width to one or more diameter or one of more of the longest dimension of a droplet formed by the concentration unit.

In one embodiment, the array further comprising at least one supporting structure positioned between the concentration units, which aids in separating, fixing, stabilizing and keeping a desired distance between the concentration units.

In one embodiment, the array further comprising at least one supporting structure positioned between the concentration units and the substrate, which aids in suspending the concentration units over the substrate, at a desired height.

In one embodiment, the supporting structure comprises a shift mechanism, wherein the shift mechanism comprises a pump, a screw, a gear, shaft, a flexible, pressed or elastic material, a wheel, a lever, a magnet, a coil, micromanipulators or a combination thereof.

In one embodiment, the shift mechanism is mechanical, pneumatic, electrical, magnetic, electrically-controlled, computerized or a combination thereof.

In one embodiment, the concentration device further comprising controllers to maintain desirable environmental conditions, wherein the environmental conditions comprises pressure, temperature, pH, $CO_2$ or Oxygen conditions, or a combination thereof.

In one embodiment, this invention provides a method for concentrating a species of interest in a liquid, the method comprising the steps of:
  introducing a liquid comprising charged species from a source into a microfluidic electrokinetic concentration device comprising:
    at least one concentration unit positioned such that at least a portion of the concentration unit is constructed within, adhered to or contiguous with a first substrate, the concentration unit comprising:
      at least one first sample microchannel through which a liquid comprising charged species can be made to pass from a first side to a second side, wherein at least a portion of the first channel is exposed to the environment;
      at least one second sample microchannel through which the liquid comprising charged species can be made to pass from a first side to a second side, wherein at least a portion of the second channel is exposed to the environment;
      at least one buffer microchannel or reservoir comprising a buffer;
      at least one conduit proximal to the sample microchannels and linked to the buffer microchannel or reservoir; and
      at least one unit to induce an electric field in the conduit, the sample microchannel, the buffer microchannel or reservoir or a combination thereof.

Such that a droplet of liquid, at least partially exposed to the environment, is brought into contact with the first sample microchannel, the second sample microchannel, and the conduit.

inducing a first electric field in the sample microchannels and in the droplet whereby electroosmotic flow is induced in the sample microchannels, the flow further introducing the liquid into the device through the sample microchannels and the flow is controlled by the strength of the first electric field; and inducing a second electric field in the conduit, whereby charged species depletion occurs in a region proximal to the conduit within the droplet and whereby the charged species are confined to another region within the droplet.

In one embodiment, liquid introduction from a source into the microfluidic device comprising the use of a pressure inducing unit, an electroosmotic flow inducing unit or a combination thereof.

In one embodiment the pressure inducing unit, the electroosmotic flow inducing unit or a combination thereof control the size of the droplet.

In one embodiment at least a portion of the concentration unit further comprises a second substrate positioned proximally to or adhered to the first substrate or a portion thereof, wherein the second substrate supports, seals and/or stabilizes at least a portion of the concentration unit In one embodiment, the first electric field in the sample microchannels and in the droplet is generated by applying a higher voltage to the first sample microchannel and a lower voltage to the second sample microchannel.

In one embodiment, the higher voltage, the lower voltage or a combination thereof is positive voltage.

In one embodiment, the positive voltage is between 50 mV and 500 V.

In one embodiment, the higher voltage is positive and the lower voltage is achieved by electrically grounding the second sample microchannel.

In one embodiment, the second electric field in the conduit is generated by applying a higher voltage to the side of the conduit that is linked to the droplet and a lower voltage to the side of the conduit that is linked to the buffer microchannel.

In one embodiment, the higher voltage is positive and the lower voltage is applied by electrically grounding the buffer microchannel or reservoir linked to the conduit.

In one embodiment, the higher voltage is the result of the two voltages applied to the first and to the second sample microchannels.

In one embodiment, the higher voltage has an intermediate value lying between the values of the two voltages applied to the first and to the second sample microchannels.

In one embodiment, the first and second electric fields are induced by applying a voltage of 400 V to the first sample microchannel and by applying a voltage of 350 V to the second sample microchannel and wherein the buffer microchannel or reservoir is electrically grounded.

In one embodiment, the droplet shape is spherical, hemispherical, or any other contour shaped.

In one embodiment, the conduit comprising a polymer-based permselective material, wherein the polymer-based permselective material comprising a cation selective or an anion selective material.

In one embodiment, the surface of the conduit and/or the sample or buffer microchannels or buffer reservoir has been functionalized to enhance the operation efficiency of the device.

In one embodiment, the device is comprised of a transparent material, wherein the transparent material comprises pyrex, silicon dioxide, polydimethylsiloxane (PDMS), silicon nitride, quartz or SU-8.

In one embodiment, the concentration device comprising an array of concentration units.

In one embodiment, the concentration units are stacked such that the two long axes of each unit are arranged in parallel to the two long axes of a neighboring concentration unit, and such that the region of the microchannels that is exposed to the environment in at least two of the units is directed to the same side with respect to the at least two concentration units.

In one embodiment, the concentration units are positioned such that the shortest axis and one of the longer axes of the units are arranged in parallel to the shortest axis and one of the longer axes of a neighboring concentration unit, and such that the region of the microchannels that is exposed to the environment in at least two of the units is directed to the same side with respect to the at least two concentration units.

In one embodiment, the droplets are on the same plane.

In one embodiment, the array is positioned on top of a substrate.

In one embodiment, the regions on the substrate that are proximal to the droplets are coated with an indicator species, capable of interacting with the charged species.

In one embodiment, the indicator species reacts with the concentrated charged species contained in the droplet.

In one embodiment, the reaction results in identification, quantification or a combination thereof of the concentrated charged species.

In one embodiment, the regions on the substrate that are proximal to the droplet are connected to a measurement device, wherein the measurement device optionally measures fluorescence.

In one embodiment, the regions on the substrate that are proximal to the droplet comprise cavities.

In one embodiment, the regions on the substrate that are proximal to the droplets fit a syringe or a dispenser array.

In one embodiment, the syringe or dispenser array is used to transfer the contents of the regions on the substrate which are proximal to the droplets to an assay system.

In one embodiment, the syringe or dispenser array is used to add assay material to the regions on the substrate that are proximal to the droplets.

In one embodiment, the spacing between rows or columns or combination thereof within the array approximates in width to one or more diameter or longest dimension of a droplet formed by the concentration unit.

In one embodiment, the array further comprising at least one supporting structure positioned between the concentration units, which aids in separating, fixing, stabilizing and keeping a desired distance between the concentration units.

In one embodiment, the array further comprising at least one supporting structure positioned between the concentration units and the substrate, which aids in suspending the concentration units over the substrate at a desired height and in bringing the concentration units in contact with the substrate.

In one embodiment, the supporting structure is used to transfer at least a portion of the droplet from the concentration unit to the substrate.

In one embodiment, the supporting structure comprises a shift mechanism, the shift mechanism comprises a pump, a screw, a gear, shaft, a flexible, pressed and/or elastic material, a wheel, a lever, a magnet, a coil, micromanipulators or a combination thereof.

In one embodiment, the shift mechanism is mechanical, pneumatic, electrical, magnetic, electrically-controlled, computerized or a combination thereof.

In one embodiment, the array comprises at least 1000 concentration units.

In one embodiment, at least a portion of the droplet comprising the confined charged species is transferred to a substrate, a vessel, a tip, a syringe, a container, a test-tube, an absorbing material, a filter paper, a column or a TLC plate.

In one embodiment, the transfer is performed by bringing the droplet into contact with the substrate, vessel, tip, syringe, container, tube, test-tube, absorbing material, filter paper, column or TLC plate; and by retrieving the substrate, vessel, tip, syringe, container, test-tube, absorbing material, filter paper, column or TLC plate.

In one embodiment, the concentration device further comprising controllers to maintain desirable environmental conditions, wherein the environmental conditions comprising pressure, temperature, pH, $CO_2$ or Oxygen conditions, or a combination thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1(*a*) is a schematic representation of the open-end preconcentration device. Two microchannels (channels 1 and 2) are connected to the outside of a PDMS chip and connected with a sample droplet. Ground channel is connected to the outside via nano-junction (a conduit). Tangential electric field ($E_T$) and normal electric field ($E_N$) were applied along the droplet and across the nanochannel, respectively. FIG. 1(*b*) is an overview of one embodiment of a device.

FIG. 2(*a*) shows experimental results using FITC fluorescence. Applied voltages are V1=400 V, V2=350 V and V3=V4=0 V. Initially no fluorescence is in the droplet (t=0 sec). The concentrated plug is formed from the channel 1 side (t=5 sec), and then inside the droplet (t=10 sec). After 15 seconds, the fluorescence is concentrated at the left side of the droplet (t=15 sec). The droplet size is increasing since the induced force of EOF is stronger than the surface tension. The bright shell in (t=10 sec) is due to reflection. FIG. 2(*b*) is an image of direct contact dispensing from PDMS to MALDI sample plate. Droplet stays on the surface of the PDMS connected to a microchannel. (t=0 sec) Upper image of the droplet is a reflection on the MALDI sample plate. The plate moved downward to form a liquid bridge (t=3 sec). The plate moves upward and liquid bridge breaks, leaving a droplet on the plate surface (t=6 sec). FIG. 2(*c*) is a plot summarizing the area of saturated brightness inside the droplet. It was first analyzed within half of the droplet (region (i)) and then to neglect the reflection near the edge, inner part of the droplet (region (ii), partial drop) was analyzed. With time, the area of saturated brightness increases, confirming the concentration process inside the droplet.

FIG. 3(a) shows integrated devices for parallel dispensing. Multiple devices or units are stacked up into one big device with different samples on the bottom. This can be connected to a motorized-stage to dispense droplets on a target surface (possibly protein/DNA microarrays). This dispensing can be done either simultaneously or separately, depending on the motorized stage configuration. FIG. 3(b) illustrates devices that are bonded to a glass plate, where analysis can be done directly on-plate.

Figure 1:
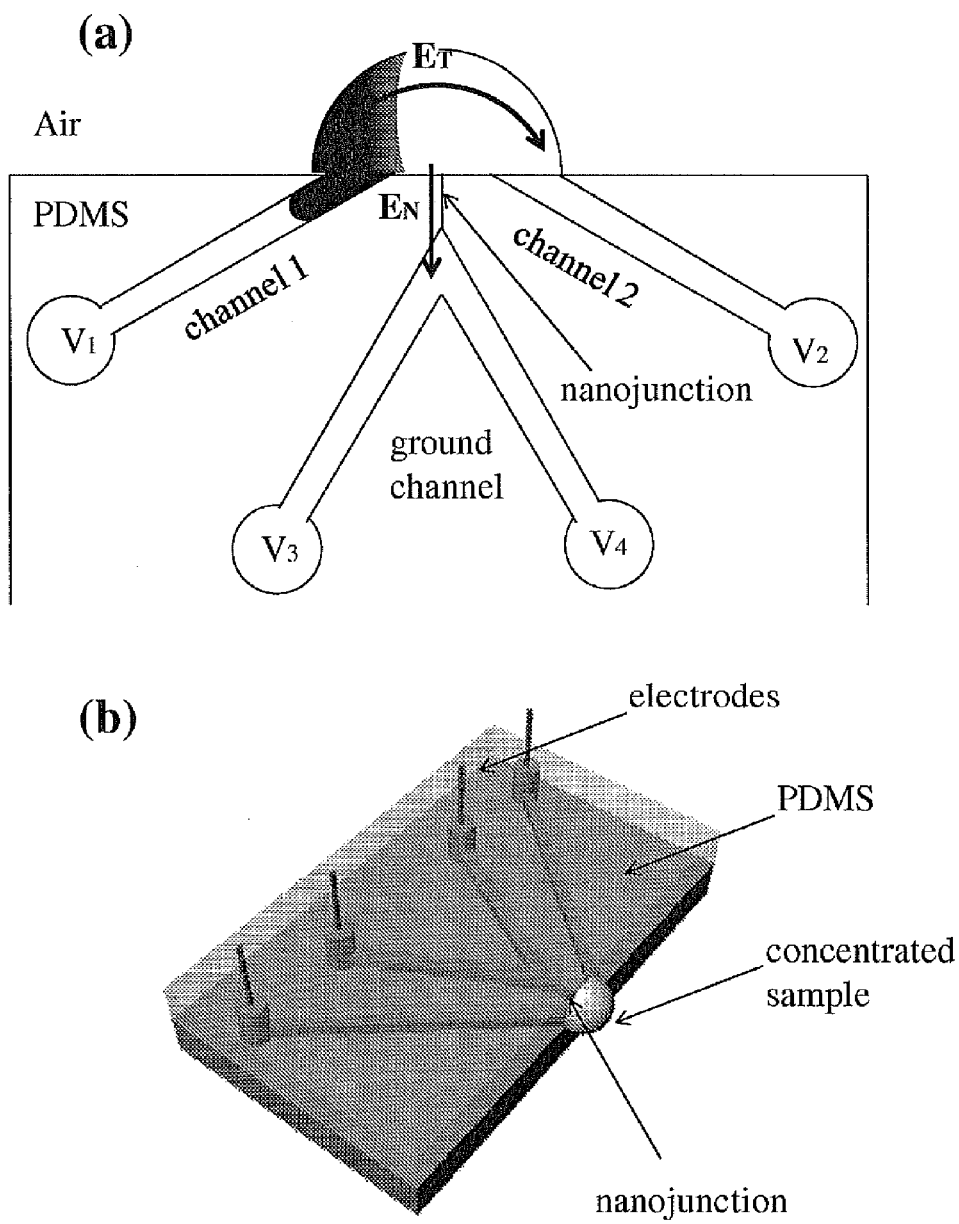
FIG. 1 is an embodiment illustrating a schematic of a device of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, this invention provides a device and methods for increasing the concentration of a charged species in solution, wherein the solution containing the concentrated species is exposed to the environment. Such solution can be formed on a surface or on a tip of a measurement device. Such solution can be delivered to a surface or to a tip of a measurement device. The open-environment concentration technique overcomes the disadvantages of in-channel concentration devices, especially by eliminating flow-induced delivery processes that lead to concentration losses. Combined with direct contact dispensing, methods of this invention can be used for various applications such as immunoassay and MALDI-MS.

In one embodiment, this invention provides an electrokinetic concentration device comprising:
  at least one concentration unit positioned such that at least a portion of the concentration unit is constructed within, adhered to or contiguous with a first substrate, the concentration unit comprising:
    at least one first sample microchannel through which a liquid comprising charged species can be made to pass from a first side to a second side, wherein at least a portion of the first channel is exposed to the environment;
    at least one second sample microchannel through which the liquid comprising charged species can be made to pass from a first side to a second side, wherein at least a portion of the second channel is exposed to the environment;
    at least one buffer microchannel or reservoir comprising a buffer;
    at least one conduit proximal to the sample microchannels and linked to the buffer microchannel or reservoir; and
    at least one unit to induce an electric field in the conduit, the sample microchannel, the buffer microchannel or reservoir or a combination thereof.

In one embodiment, the sample microchannels comprise liquid or solution comprising a charged species of interest and the concentration unit comprises a droplet of the liquid or solution, wherein the droplet is at least partially exposed to the environment and wherein the droplet is in contact with the sample microchannels and the conduit.

In one embodiment, the droplet comprises liquid. In one embodiment, the liquid in the droplet is in contact with the liquid in the sample microchannels, the liquid in the conduit or a combination thereof. In one embodiment, a continuous liquid system is provided, the liquid system comprising the liquid in the first and the second sample microchannels, the liquid in the droplet and the liquid in the conduit.

In one embodiment, at least a portion of the concentration unit is positioned proximally to or adhered to a plate. In one embodiment, the plate is a glass plate. In one embodiment, the plate is made out of metal, metal oxide, polymer, quartz or pyrex. In one embodiment, the plate is made of an insulating, semiconducting or conducting material. In one embodiment, the plate comprises a microfluidic device as well. In one embodiment, the plate comprises cavities, depressions, or holes that fit the droplet area of the concentration units. In one embodiment, the plate is part of a measurement device. In one embodiment, the plate is rough. In one embodiment, the plate is smooth. In one embodiment, the plate is disposable.

In one embodiment, the plate support, seals and/or stabilizes at least a portion of the concentration unit.

In one embodiment, the plate is in contact with the droplet.

In one embodiment, the width of the sample microchannels, the buffer microchannel or a combination thereof is between 1-100 μm.

In one embodiment, the depth of the sample microchannels, the buffer microchannel or a combination thereof is between 0.5-50 μm.

In one embodiment, the width of the conduit is between 100-4000 nanometers. In one embodiment, the width of the conduit is between 1-100 micrometers. In one embodiment, the depth of the conduit is between 20-100 nanometers. In one embodiment, the depth of the conduit is between 1-100 micrometers. In one embodiment, the conduit is a nanochannel.

In one embodiment, the droplet diameter or droplet longest dimension ranges between 400 micrometers and 1000 micrometers.

In one embodiment, the droplet longest dimension ranges between 1 micrometer and 500 micrometers. In one embodiment, the droplet longest dimension ranges between 0.01 micrometer and 1 micrometer. In one embodiment, the droplet longest dimension ranges between 50 micrometer and 150 micrometers. In one embodiment, the droplet longest dimension ranges between 100 micrometer and 400 micrometers. In one embodiment, the droplet longest dimension ranges between 600 micrometer and 800 micrometers.

Figure 2:
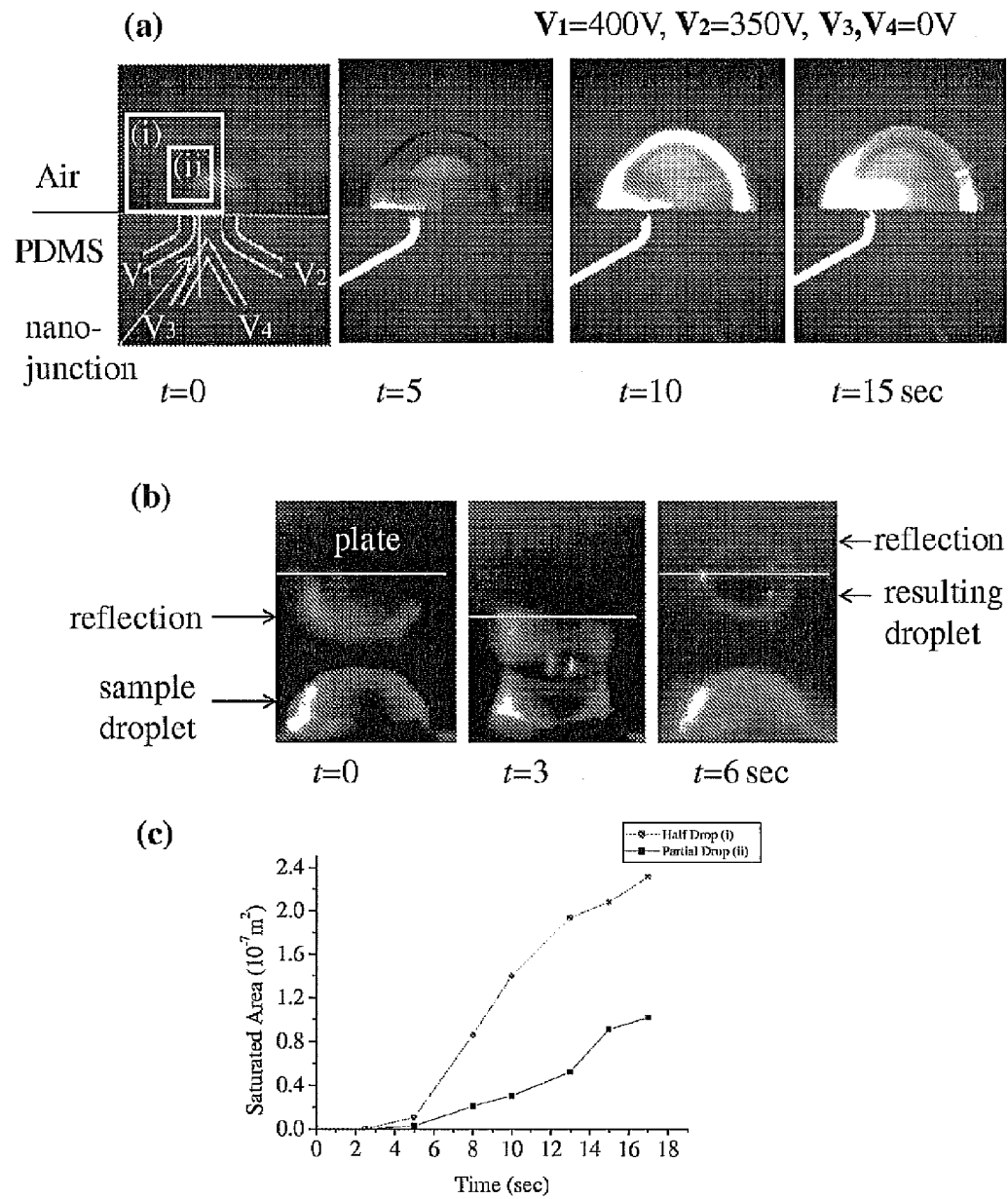
FIG. 2 illustrates the results of one embodiment of a method of concentrating a species in a liquid.

In one embodiment, the droplet shape is spherical, hemispherical, or any other contour shaped. In one embodiment, the droplet shape depends on the surface tension of the liquid/solution. In one embodiment, the contact angle between the droplet and the surface of the concentration unit varies between 1 degree and 120 degrees. In one embodiment, the contact angle can be modified by modifying the surface of the concentration unit. In one embodiment, the droplet shape depends on the environmental conditions such as pressure, temperature and humidity. In one embodiment, droplet size does not change during the concentration process. In one embodiment, droplet size increases or decreases during the concentration process. In one embodiment, the electric field induced in the concentration unit affects the size of the droplet. In one embodiment, droplet size ranges between 650 µm and 780 µm. In one embodiment, droplet size ranges between 500 µm and 1000 µm. In one embodiment, droplet size ranges between 50 µm and 500 µm. In one embodiment, droplet size ranges between 100 µm and 400 µm. In one embodiment, droplet size ranges between 750 µm and 2000 µm. In one embodiment, droplet size ranges between 200 µm and 1000 µm. In one embodiment, droplet size ranges between 10 µm and 100 µm. In one embodiment, the droplet bridges between the surface of the concentration unit and an additional surface that is in contact with the drop. In one embodiment, the shape of the bridging droplet is as depicted in FIG. 2 at t=3. In one embodiment, the shape of the bridging droplet is such that at the center, the droplet is thinner than at the edges. In one embodiment, the shape of the droplet depends on the distance between the two surfaces which are in contact with the droplet.

In one embodiment, the separation between the exposed portions of the first sample microchannel and the second sample microchannel ranges between 50 micrometers and 1000 micrometers. In one embodiment, the separation between the exposed ends ranges between 0.01 micrometers and 1 micrometer. In one embodiment, the separation between the exposed ends ranges between 1 micrometers and 100 micrometers. In one embodiment, the separation between the exposed ends ranges between 50 micrometers and 500 micrometers. In one embodiment, the separation between the exposed ends ranges between 150 micrometers and 750 micrometers.

In one embodiment, the separation between the exposed ends of the two sample microchannels is smaller than any dimension of the surface that is covered by the droplet. In one embodiment, the separation between the exposed ends of the two sample microchannels is larger than any dimension of the surface that is covered by the droplet. In one embodiment, the separation between the exposed ends of the two sample microchannels is smaller than at least one dimension of the surface that is covered by the droplet. In one embodiment, the separation between the exposed ends of the two sample microchannels is larger than at least one dimension of the surface that is covered by the droplet. In one embodiment, the separation between the exposed ends of the two sample microchannels is equal to a dimension of the surface that is covered by the droplet.

In one embodiment, the conduit comprising a polymer-based permselective material.

In one embodiment, one end of each of the sample microchannel is at the edge of the substrate in or on which the microchannels are constructed. In one embodiment, the ends of the two microchannels that are at the edge as depicted in FIG. 1, are exposed to the environment. In one embodiment, the two microchannels or portions thereof are not parallel. In one embodiment, there is an angle between the two microchannels. In one embodiment, the angle between the lengths of the two microchannels or portions thereof ranges between 90 degrees and 180 degrees. In one embodiment, the angle between the lengths of the two microchannels or portions thereof ranges between zero degrees and 90 degrees. In one embodiment, the conduit is placed exactly or approximately in the center of the area between the two microchannels. In one embodiment, the conduit is not placed at the center between the two microchannels, but rather it is placed closer to one microchannel and more distant from the other microchannel. In one embodiment, the length of the conduit or portions thereof is perpendicular or approximately perpendicular to the substrate edge (see e.g. FIG. 1). In one embodiment, the conduit is not perpendicular to the edge of the substrate. In one embodiment, there is an angle between the conduit and the edge of the substrate. In one embodiment, such angle ranges between zero degrees and 90 degrees. In one embodiment, the term approximately means±10% of the value described. In one embodiment, approximately means±15% of the value described. In one embodiment, approximately means±20% of the value described. In one embodiment, approximately means±5% of the value described.

In one embodiment, the conduit comprises ion-selective membrane comprising polytetrafluorethylenes (PTFEs), perfluorosulfonates, polyphosphazenes, polybenzimidazoles (PBIs), poly-zirconia, polyethyleneimine-poly(acrylic acid), poly(ethylene oxide)-poly(acrylic acid), non-fluorinated hydrocarbon polymers or polymer-inorganic composites. In some embodiments the ion selective membrane comprises sulfonated tetrafluoroethylene copolymer. In some embodiments the sulfonated tetrafluoroethylene copolymer comprises Nafion solution. In some embodiments the ion selective membrane comprises microparticles or beads. In some embodiments the microparticles or beads comprises silica or polystyrene.

In one embodiment, the polymer-based permselective material comprising Nafion. In one embodiment, the polymer-based permselective material comprising a cation selective or an anion selective material.

In one embodiment, the conduit comprising an electrical junction that is preferentially conductive to positive ions or to negative ions. In one embodiment, conductive means electrical conductance. In one embodiment, conductive means that the ions can move, migrate, relocate or flow through the junction.

In one embodiment, the surface of the sample microchannels has been functionalized to reduce adsorption of species of interest to the surface. In one embodiment, functionalization comprises coating with extracellular matrix protein's, amino acids, PEG, or PEG functionalized SAM's or by a slightly charged species to prevent adhesion of cells or cellular material to the surface. In another embodiment, functionalization comprises treatment of a surface to minimize, reduce or prevent background fluorescence. Such functionalization may comprise, for example, inclusion of anti-quenching materials, as are known in the art. In another embodiment, the functionalization may comprise treatment with specific materials to alter flow properties of the material through the device. In another embodiment, such functionalization may be in discrete regions, randomly, or may entirely functionalize an exposed surface of a device of this invention.

In one embodiment, the surface of the conduit and/or the sample or buffer microchannels or buffer reservoir has been functionalized to enhance the operation efficiency of the device.

In one embodiment, an external gate voltage is applied to the substrate of the device, to enhance the operation efficiency of the device.

In one embodiment, the sample microchannels, the buffer microchannel or buffer reservoir, the conduit or combination thereof, are formed by lithography and etching processes. In one embodiment, the device is comprised of a transparent material. In one embodiment, the transparent material is pyrex, silicon dioxide, polydimethylsiloxane (PDMS), silicon nitride, quartz or SU-8. In one embodiment, the device is coated with a low-autofluorescent material. In one embodiment, the device is coupled to a pump. In one embodiment, the device is coupled to a sensor, separation system, detection system, analysis system or combination thereof. In one embodiment, the detection system comprises an illumination source, a camera, a computer, a luminometer, a spectrophotometer, or a combination thereof.

In one embodiment, the liquid flow speed in the sample microchannel is between 100 µm/sec and 10 mm/sec. In one embodiment, the liquid flow speed in the sample microchannel is between 1 µm/sec and 100 µm/sec. In one embodiment, the liquid flow speed in the sample microchannel is between 0.1 µm/sec and 10 µm/sec. In one embodiment, the liquid volume flow rate is at least 1 L/min. In one embodiment, the liquid volume flow rate ranges between 60-100 L/min. In one embodiment, the liquid volume flow rate ranges between 1 µL/min and 1 mL/min. In one embodiment, the liquid volume flow rate ranges between 1 mL/min and 1 L/min.

In one embodiment, the concentration device comprising an array of concentration units.

In one embodiment, the concentration units of the array are stacked such that the two long axes of each unit are arranged in parallel to the two long axes of a neighboring concentration unit, and such that the region of the microchannels that is exposed to the environment in at least two of the units is directed to the same side with respect to the at least two concentration units.

In one embodiment, the concentration units of the array are positioned such that the shortest axis and one of the longer axes of the units are arranged in parallel to the shortest axis and one of the longer axes of a neighboring concentration unit, and such that the region of the microchannels that is exposed to the environment in at least two of the units is directed to the same side with respect to the at least two concentration units.

Figure 3:
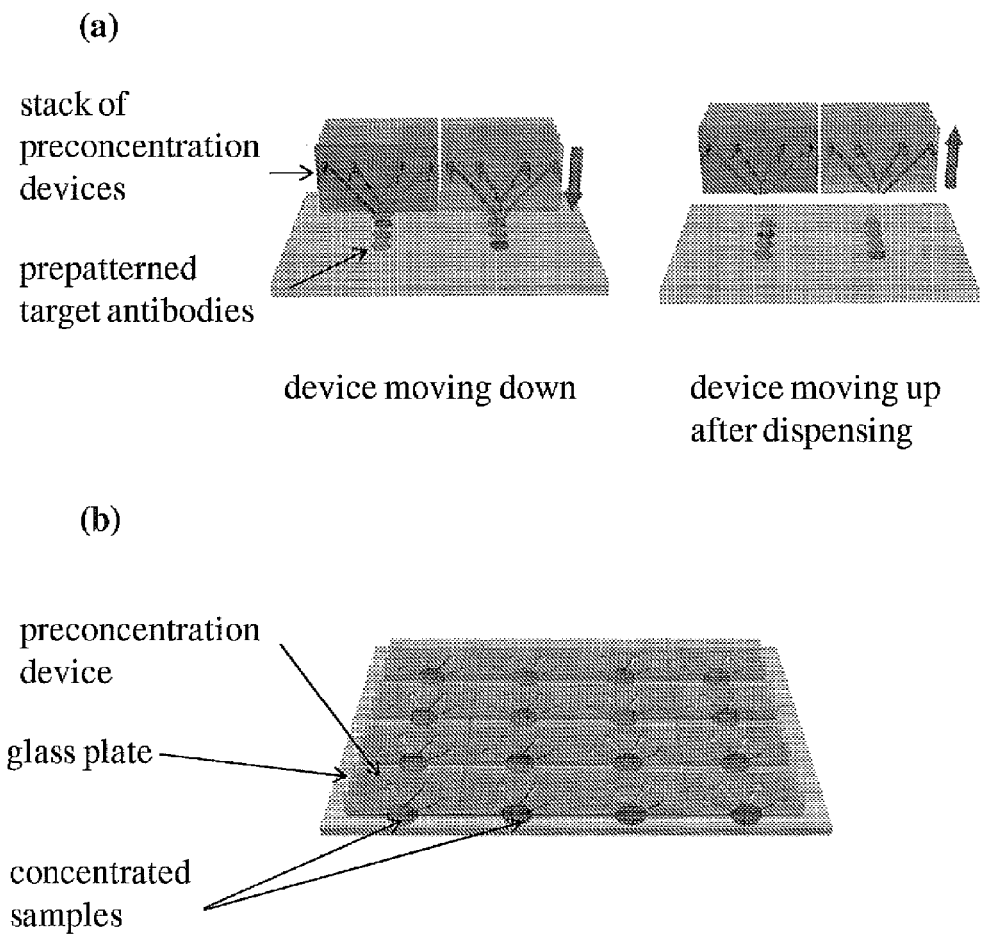
FIG. 3 illustrates an embodiment of a schematic diagram of integrated system.

In one embodiment, the droplets are on the same plane. In one embodiment, when droplets are on the same plane they can be used in parallel for an assay as depicted in FIG. 3 in one embodiment. In one embodiment, when droplets are on the same plane they can be transferred at the same time to an assay substrate as depicted in FIG. 3 (b) in one embodiment.

In one embodiment, the array is positioned on top of a substrate. In one embodiment, the array is fixed to the substrate. In one embodiment, the droplets are temporarily in contact with the substrate.

In one embodiment, the regions on the substrate that are proximal to the droplets are coated with an indicator species, capable of interacting with the charged species. In one embodiment, the indicator species reacts with the concentrated charged species contained in the droplet.

In one embodiment, the reaction results in identification of the concentrated charged species. In one embodiment, the reaction results in quantification of the concentrated charged species.

In one embodiment, the regions on the substrate that are proximal to the droplet are spectrally monitored. In one embodiment, the regions on the substrate that are proximal to the droplet are connected to a measurement device. In one embodiment, the measurement device measures fluorescence.

In one embodiment, the regions on the substrate that are proximal to the droplet comprise cavities.

In one embodiment, the regions on the substrate that are proximal to the droplets fit a syringe or a dispenser array.

In one embodiment, the syringe or dispenser array is used to transfer the contents of the regions on the substrate which are proximal to the droplets to an assay system. In one embodiment, the syringe or dispenser array is used to add assay material to the regions on the substrate that are proximal to the droplets.

In one embodiment, the regions on the substrate that are proximal to the droplet are as depicted in FIG. 3. In one embodiment, the regions proximal to the droplet are in contact with the droplet or with portions thereof. In one embodiment, the regions proximal or close to or adjacent or neighboring to the droplet, are regions on the substrate that may be in contact with the droplet during a certain period of time in the process and are not in contact with the droplet during another period of time in processes of this invention. In one embodiment, during species concentration, the regions proximal to the droplet on the substrate are not in contact with the droplet, and after concentration, the droplet is brought into contact with the regions on the substrate that are proximal to the droplet. In one embodiment, the regions on the substrate that are proximal to the droplet, are in contact with the droplet during the concentration process. In one embodiment, the substrate with the regions that are proximal to the droplet can be detached from the concentration unit array and can be transferred to a measurement or to an analysis system.

In one embodiment, the array is disposable.

In one embodiment, the spacing between rows or columns or combination thereof within the array approximates in width to one or more diameter or one of more of the longest dimension of a droplet formed by the concentration unit.

In one embodiment, the concentration device further comprises controllers to maintain desirable environmental conditions. In one embodiment, the controllers maintain a desired pressure, temperature, pH, $CO_2$ or Oxygen conditions, or a combination thereof.

In one embodiment, the array further comprising at least one supporting structure positioned between the concentration units, which aids in separating, fixing, stabilizing and keeping a desired distance between the concentration units.

In one embodiment, the array further comprising at least one supporting structure positioned between the concentration units and the substrate, which aids in suspending the concentration units over the substrate, at a desired height.

In one embodiment, the supporting structure comprises a shift mechanism. In one embodiment, the shift mechanism comprises a pump, a screw, a gear, shaft, a flexible, pressed or elastic material, a wheel, a lever, micromanipulators or a combination thereof. In one embodiment, the shift mechanism is mechanical, pneumatic, electrical, magnetic, electrically-controlled, computerized or a combination thereof. In one embodiment, the supporting structure can shift the array with respect to a substrate such that the droplets on the array, form contact with the substrate upon lowering of the device, and portions of the droplets are left on the substrate when the supporting structure lifts the array to the point where the droplet divides between the substrate and the array. In one embodiment, instead of or in addition to a supporting structure, the contact and retrieval of the droplets is performed manually.

In one embodiment, the concentration device further comprises electrical connections between the first sample microchannel, the second sample microchannel, the buffer microchannel or reservoir, the conduit or a combination thereof and a power supply.

In one embodiment, the array comprises at least 1000 concentration units. In one embodiment, the device length, width, height or a combination thereof ranges between 10 cm to 30 cm.

In one embodiment, the device is part of an apparatus. In one embodiment, the apparatus is handheld/portable. In one embodiment, the apparatus is a table top apparatus.

In one embodiment, this invention provides a method for concentrating a species of interest in a liquid, the method comprising the steps of:

introducing a liquid comprising charged species from a source into a microfluidic device comprising:

at least one concentration unit positioned such that at least a portion of the concentration unit is constructed within, adhered to or contiguous with a first substrate, the concentration unit comprising:

at least one first sample microchannel through which a liquid comprising charged species can be made to pass from a first side to a second side, wherein at least a portion of the first channel is exposed to the environment;

at least one second sample microchannel through which the liquid comprising charged species can be made to pass from a first side to a second side, wherein at least a portion of the second channel is exposed to the environment;

at least one buffer microchannel or reservoir comprising a buffer;

at least one conduit proximal to the sample microchannels and linked to the buffer microchannel or reservoir; and at least one unit to induce an electric field in the conduit, the sample microchannel, the buffer microchannel or reservoir or a combination thereof.

Such that a droplet of liquid, at least partially exposed to the environment, is brought into contact with the first sample microchannel, the second sample microchannel, and the conduit.

inducing a first electric field in the sample microchannels and in the droplet whereby electroosmotic flow is induced in the sample microchannels and in the droplet, the flow further introducing the liquid into the device through the sample microchannels and the flow is controlled by the strength of the first electric field; and inducing a second electric field in the conduit, whereby charged species depletion occurs in a region proximal to the conduit within the droplet and whereby the charged species are confined to another region within the droplet.

In one embodiment, the liquid introduction from a source into the microfluidic device comprises the use of a pressure inducing unit, an electroosmotic flow inducing unit or a combination thereof.

In one embodiment, the pressure inducing unit, the electroosmotic flow inducing unit or a combination thereof control the size of the droplet.

In one embodiment, at least a portion of the concentration unit further comprises a second substrate positioned proximally to or adhered to the first substrate or a portion thereof.

In one embodiment, the second substrate is a glass plate. In one embodiment, the plate supports, seals and/or stabilizes at least a portion of the concentration unit. In one embodiment, the glass plate is in contact with the droplet.

In one embodiment, the first electric field in the sample microchannels and in the droplet is generated by applying a higher voltage to the first sample microchannel and a lower voltage to the second sample microchannel.

In one embodiment, the higher voltage, the lower voltage or a combination thereof is positive voltage.

In one embodiment, the positive voltage is between 50 mV and 500 V. In one embodiment, the positive voltage is between 50 V and 200 V. In one embodiment, the positive voltage is between 300 mV and 1000 V. In one embodiment, the positive voltage is between 10 mV and 100 V.

In one embodiment, the higher voltage is positive and the lower voltage is achieved by electrically grounding the second sample microchannel. In one embodiment, the second electric field in the conduit is generated by applying a higher voltage to the side of the conduit that is linked to the droplet and a lower voltage to the side of the conduit that is linked to the buffer microchannel. In one embodiment, the higher voltage is positive and the lower voltage is applied by electrically grounding the buffer microchannel or reservoir linked to the conduit. In one embodiment, the higher voltage is the result of the two voltages applied to the first and to the second sample microchannels. In one embodiment, the higher voltage has an intermediate value lying between the values of the two voltages applied to the first and to the second sample microchannels.

In one embodiment, the first and second electric fields are induced by applying a voltage of 400 V to the first sample microchannel and by applying a voltage of 350 V to the second sample microchannel and wherein the buffer microchannel or reservoir is electrically grounded.

In one embodiment, the width of the sample microchannels, the buffer microchannel or a combination thereof is between 1-100 μm. In one embodiment, the depth of the sample microchannels, the buffer microchannel or a combination thereof is between 0.5-50 μm.

In one embodiment, the width of the conduit is between 100-4000 nanometers. In one embodiment, the width of the conduit is between 1-100 micrometers. In one embodiment, the depth of the conduit is between 20-100 nanometers. In one embodiment, the depth of the conduit is between 1-100 micrometers.

In one embodiment, the conduit is a nanochannel.

In one embodiment, the droplet diameter or droplet longest dimension ranges between 400 micrometers and 1000 micrometers.

In one embodiment, the droplet shape is spherical, hemispherical, or any other contour shaped.

In one embodiment, the separation between the exposed portions of the first sample microchannel and the second sample microchannel ranges between 50 micrometers and 1000 micrometers.

In one embodiment, the conduit comprising a polymer-based permselective material. In one embodiment, the polymer-based permselective material comprising Nafion. In one embodiment, the polymer-based permselective material comprising a cation selective or an anion selective material.

In one embodiment, the conduit comprising an electrical junction that is preferentially conductive to positive ions or to negative ions.

In one embodiment, the conduit comprising a nanoporous structure made from closed-packed microbeads or nanobeads, which may or may not be coated with a cation selective or an anion selective material. In one embodiment, microbeads are beads having a diameter ranging between 1 micrometer and 1000 micrometers. In one embodiment, nanobeads are beads having a diameter ranging between 1 nanometer and 1000 nanometers. In one embodiment, beads are spheres or clusters or nano- or micro-particles. In one embodiment, beads are made of polystyrene or silica.

In one embodiment, the surface of the sample microchannels has been functionalized to reduce adsorption of species of interest to the surface. In one embodiment, the surface of the conduit and/or the sample or buffer microchannels or buffer reservoir has been functionalized to enhance the operation efficiency of the device.

In one embodiment, an external gate voltage is applied to the substrate of the device, to enhance the operation efficiency of the device.

In one embodiment, the sample microchannels, the buffer microchannel or buffer reservoir, the conduit or combination thereof, are formed by lithography and etching processes.

In one embodiment, the device is comprised of a transparent material. In one embodiment, the transparent material is pyrex, silicon dioxide, polydimethylsiloxane (PDMS), silicon nitride, quartz or SU-8.

In one embodiment, the device is coated with a low-autofluorescent material.

In one embodiment, the device is coupled to a pump. In one embodiment, the device is coupled to a sensor, separation system, detection system, analysis system or combination thereof.

In one embodiment, introducing a liquid into the microfluidic device is done by introducing the liquid into the microchannels and into the conduit. In one embodiment, introduction of liquid into the channels is conducted using a pump, a syringe, an automated injection system, through a reservoir, through a guide channel, through a guiding tube, using force, manually or automatically. In one embodiment, the pressure applied to the liquid for introduction into the microchannels and/or the conduit is controlled. In one embodiment, negative or positive pressures or a combination thereof are utilized for introducing liquid into the channels of the device. In one embodiment, when liquid emerges from a second side of the first microchannel or from a first side of the second microchannel, a droplet is formed outside the ends of a second side of the first microchannel and on a first side of the second microchannel.

In one embodiment, the detection system comprises an illumination source, a camera, a computer, a luminometer, a spectrophotometer, or a combination thereof.

In one embodiment, the liquid flow speed in the sample microchannel is between 100 μm/sec and 10 mm/sec.

In one embodiment, the liquid volume flow rate is at least 1 L/min. In one embodiment, the liquid volume flow rate ranges between 60-100 L/min.

In one embodiment, the concentration device comprising an array of concentration units.

In one embodiment, the concentration units are stacked such that the two long axes of each unit are arranged in parallel to the two long axes of a neighboring concentration unit, and such that the region of the microchannels that is exposed to the environment in at least two of the units is directed to the same side with respect to the at least two concentration units.

In one embodiment, the concentration units are positioned such that the shortest axis and one of the longer axes of the units are arranged in parallel to the shortest axis and one of the longer axes of a neighboring concentration unit, and such that the region of the microchannels that is exposed to the environment in at least two of the units is directed to the same side with respect to the at least two concentration units.

In one embodiment, the droplets are on the same plane.

In one embodiment, the array is positioned on top of a substrate. In one embodiment, the array is fixed to the substrate. In one embodiment, the droplets are temporarily in contact with the substrate.

In one embodiment, the regions on the substrate that are proximal to the droplets are coated with an indicator species, capable of interacting with the charged species. In one embodiment, the indicator species reacts with the concentrated charged species contained in the droplet. In one embodiment, the reaction results in identification of the concentrated charged species. In one embodiment, the reaction results in quantification of the concentrated charged species.

In one embodiment, the concentrated species in the droplet is reacted with a ligand, a protein ligand an antibody, a fluorescent marker, a nucleic acid, an enzyme, an atom, a molecule, an ion, a saccharide, a radioactive molecule, a dye molecule, a nanoparticle or a combination thereof.

In one embodiment, the reaction may be conducted by adding the above-mentioned material into the droplet, or by dispensing the droplet onto a substrate wherein the material of interest is placed before or after droplet content dispensing. In one embodiment, the concentrated species in the droplet is transferred upon contact to another substrate where a reaction with another species takes place. In one embodiment, the concentrated species in the droplet is transferred by suction to another container, microwell, vessel, tube that holds the species that interacts with the concentrated species in the droplet. In one embodiment, the species to be reacted with the concentrated species in the droplet (e.g. ligand, antibody, molecule as described above) is added to the reaction container before the concentrated species is added to the container. In one embodiment, the species to be reacted with the concentrated species in the droplet (e.g. ligand, antibody, molecule as described above) is added to the reaction container after the concentrated species is added to the container.

In one embodiment, the regions on the substrate that are proximal to the droplet are spectrally monitored. In one embodiment, the regions on the substrate that are proximal to the droplet are connected to a measurement device. In one embodiment, the measurement device measures fluorescence.

In one embodiment, the regions on the substrate that are proximal to the droplet comprise cavities.

In one embodiment, the regions on the substrate that are proximal to the droplets fit a syringe or a dispenser array. In one embodiment, the syringe or dispenser array is used to transfer the contents of the regions on the substrate that are proximal to the droplets to an assay system. In one embodiment, the syringe or dispenser array is used to add assay material to the regions on the substrate that are proximal to the droplets.

In one embodiment, the array is disposable.

In one embodiment, the spacing between rows or columns or combination thereof within the array approximates in width to one or more diameter or longest dimension of a droplet formed by the concentration unit.

In one embodiment, concentration devices of this invention are called "preconcentrators".

In one embodiment, the concentration device further comprising controllers to maintain desirable environmental conditions. In one embodiment, the controllers maintain a desired pressure, temperature, pH, $CO_2$ or Oxygen conditions, or a combination thereof.

In one embodiment, the array further comprising at least one supporting structure positioned between the concentration units, which aids in separating, fixing, stabilizing and keeping a desired distance between the concentration units.

In one embodiment, the array further comprising at least one supporting structure positioned between the concentration units and the substrate, which aids in suspending the concentration units over the substrate at a desired height and in bringing the concentration units in contact with the substrate.

In one embodiment, the supporting structure is used to transfer at least a portion of the droplet from the concentration unit to the substrate.

In one embodiment, the supporting structure comprises a shift mechanism. In one embodiment, the shift mechanism comprises a pump, a screw, a gear, shaft, a flexible, pressed and/or elastic material, a wheel, a lever, micromanipulators or a combination thereof. In one embodiment, the shift mechanism is mechanical, pneumatic, electrical, magnetic, electrically-controlled, computerized or a combination thereof.

In one embodiment, the microfluidic device further comprising electrical connections between the first sample microchannel, the second sample microchannel, the buffer microchannel or reservoir, the conduit or a combination thereof and a power supply.

In one embodiment, the array comprises at least 1000 concentration units. In one embodiment, the microfluidic device length, width, height or a combination thereof ranges between 10 cm to 30 cm. In one embodiment, the microfluidic device length, width, height or a combination thereof ranges between 1 cm and 10 cm. In one embodiment, the microfluidic device length, width, height or a combination thereof ranges between 1 mm and 1 cm.

In one embodiment, the microfluidic device is part of an apparatus. In one embodiment, the apparatus is handheld/portable. In one embodiment, the apparatus is a table top apparatus.

In one embodiment, at least a portion of the droplet comprising the confined charged species is transferred to a substrate, a vessel, a tip, a syringe, a container, a test-tube, an absorbing material, a filter paper, a column or a TLC plate.

In one embodiment, the transfer is performed by bringing the droplet into contact with the substrate, vessel, tip, syringe, container, test-tube, absorbing material, filter paper, column or TLC plate; and by retrieving the substrate, vessel, tip, syringe, container, test-tube, absorbing material, filter paper, column or TLC plate. In one embodiment, the droplet is transferred to the materials and tools described herein above for the purpose of analysis and/or synthesis.

In one embodiment, the transfer process is repeated. In one embodiment, the transfer is performed in parallel for a complete array of droplets. In one embodiment, assay of a complete array of droplets is done simultaneously. In one embodiment, such process is fast, is of low-cost and is highly efficient.

I. DEFINITIONS

In one embodiment, a microfluidic device is a device comprising features with dimensions in the micron scale. In one embodiment, a microfluidic device is a device comprising features with at least one dimension between 1 micrometer (1 µm) and 1000 micrometer (1000 µm). In one embodiment, a microfluidic device is a device comprising features with dimensions in the nanometer scale. In one embodiment, a microfluidic device is a device comprising features with at least one dimension between 1 nanometer (1 nm) and 1000 nanometer (1000 nm). In one embodiment, a microfluidic device comprises channels with width or depth in the nanometer scale and with length in the micron, millimeter or centimeter scale. In one embodiment, a microfluidic device comprises channels with width or depth in the micron scale and with length in the micron, millimeter or centimeter scale. In one embodiment, such channels are referred to as microchannels.

In one embodiment, a concentration device is a device that can be used to concentrate a species in a liquid. In one embodiment, concentrating means increasing the number of species units per unit volume. In one embodiment, an electrokinetic concentration device is a concentration device wherein the concentration action is induced by an electrokinetic mechanism. In one embodiment, fluid flow, species accumulation, barrier to species movement, depletion of species from a certain region or a combination thereof is induced electrokinetically. In one embodiment, electrokinetic action involves the movement of fluid or species in response to an electric field.

In one embodiment, a concentration unit is a unit in which a species of interest in a liquid is being concentrated. In a preferred embodiment, the concentrated region of the species is within a droplet. In one embodiment, the droplet is partially exposed to the environment.

In one embodiment, liquid can be made to pass through the microchannels or through other features in a microfluidic device. In one embodiment, a microfluidic device is a device through which fluid can be made to pass. In one embodiment, fluid can be a liquid. In one embodiment, the liquid can be pure. In one embodiment, the liquid can be a mixture. In one embodiment, the liquid can be a solution. In one embodiment, the solution can contain molecules or ions. In one embodiment, the solution can be aqueous or organic. In one embodiment, an aqueous solution containing ions can be a salt solution. Solution may comprise any alkali metal salt. In one embodiment the salt comprises an alkaline earth cation. In one embodiment, the salt comprises halogen ions. In one embodiment, the salt comprises complex ions. In one embodiment, the salt or charged species comprises ions of $H^+$, $Li^+$, $Na^+$, $K^+$, $Me^+$, $Ca^{2+}$, $Fe^{2+/3+}$, $Cu^{2+}$, $Ba^{2+}$, $Au^{3+}$, $F^-$, $Br^-$, $Cl^-$, $I^-$, $OH^-$, $NO_3$, $CO_3^{2-}$, $SO_4^{2-}$ or a combination thereof. In one embodiment, the solution is a buffered solution. In one embodiment, a buffered solution is a solution that resists pH changes. In one embodiment, a buffer or a buffer solution is a solution that contains a mixture of a weak acid and its conjugate base or a weak base and its conjugate acid. In one embodiment, buffer solutions are used to stabilize biomolecules present in a solution.

In one embodiment, the liquid comprises charged species. In one embodiment, charged means electrically charged. In one embodiment, charged species is a species that can be influenced by an electric field. In one embodiment, a charged species can be forced to migrate in an electric field. In one embodiment, a charged species is attracted to a region with an opposite charge. In one embodiment, charged species migrate toward a region or a pole with an opposite charge, and are repelled or migrate away from regions with the same charge. In one embodiment, the charged species is a molecule, an ion, a particle, a cluster or an aggregate carrying an extra charge. In one embodiment, charged species is a species that is not electrically neutral. In one embodiment, the charged species is an amino acid, a peptide, a protein, a nucleotide, a DNA or RNA segment, a nanoparticle, a microparticle, a bead. In one embodiment, the charged species is a biomolecule. In one embodiment, a mixture of biomolecules can be made to pass through the microfluidic device or features thereof. In one embodiment, the mixture of biomolecules may contain charged and uncharged species. In on embodiment the mixture of biomolecules may comprise charged and uncharged biomolecules, highly and low-charged biomolecules, and a mixture of biomolecules wherein each molecule or molecule group vary in charge with respect to another molecule or with respect to another group of molecules. In one embodiment, the biomolecules and/or other charged species are present in a buffer solution.

In one embodiment, a substrate is the supporting structure of a microfluidic device. In one embodiment, the substrate is the material on which or in which the microfluidic device is built. In one embodiment, the substrate is a piece of material from which the device or portions of it will be made. In one embodiment, the substrate or the device is comprised of a transparent material. In one embodiment, the transparent material is pyrex, silicon dioxide, silicon nitride, quartz, polydimethylsiloxane (PDMS) or SU-8. In one embodiment, the device is coated with a low-autofluorescent material. In one embodiment, the substrate, the device or portions of the device are made of silicon. In one embodiment, the substrate, the device or portions of the device are made of a polymer. In one embodiment, the polymer is PDMS. In one embodiment, the substrate is planar. In one embodiment, the substrate may be curved, pointed, in the shape of a syringe or a tip, triangular shaped and/or shaped to fit a desired region in or on a measurement device. In one embodiment, the substrate shape is designed so that dispensing a droplet from a region of the substrate onto another surface is facilitated.

In one embodiment, a reservoir is any container that can hold liquids. In one embodiment, a reservoir is a vessel. In one embodiment, the reservoir has a channel structure. In one embodiment, any reservoir of the invention or the buffer reservoir or the buffer channel is rounded. In one embodiment, the reservoir or the buffer channel has two ends. In one embodiment, different or equal voltages can be applied to the two ends of the reservoir or the buffer channel. In one embodiment, the reservoir is the buffer microchannel. In one embodiment, the buffer microchannel or the reservoir are grounded using one electrode. In one embodiment, the reservoir or the buffer channel are grounded using two or more electrodes. In one embodiment, any voltage can be applied to the buffer reservoir or to the buffer microchannel or to any reservoir of the invention using one or more electrodes.

In one embodiment a conduit has at least one nanometer dimension. In one embodiment, the conduit has a thickness ranging between 1 nm and 1000 nm. In one embodiment, the conduit has dimensions in the micron scale, but has pores in the nanometer scale. In one embodiment, nanometer-sized pores are permeable. In one embodiment, nanometer-sized pores are interconnected. In one embodiment, a conduit is a nanochannel.

In one embodiment, an electric field is the space surrounding an electric charge. In one embodiment, the electric field exerts a force on other electrically charged objects. In one embodiment, a stationary charged particle in an electric field experiences a force proportional to its charge. In one embodiment, an electric field can be induced by applying a voltage. In one embodiment, an electric field can be induced in the area between two electrodes to which an unequal voltage is applied. In one embodiment, certain distribution of positive or negative charges in space can give rise to an electric field.

In one embodiment, electroosmotic flow or electro-osmotic flow, often abbreviated EOF is the motion of ions in a solvent environment through very narrow channels, where an applied voltage across the channels causes the ion migration. In one embodiment, an ion depletion zone is a region in the solution that is depleted of ions. In one embodiment, under the influence of a certain electric field, ions migrate away from the depletion zone. In one embodiment, the depletion zone contains no ions. In one embodiment, the depletion zone contains a very low concentration of ions. In one embodiment, the depletion zone contains less ions than the number of ions that were present in this zone prior to inducing the electric field. In one embodiment, the ion depletion zone in the sample microchannels or in the droplet or in the area proximal to the sample microchannels, is the region proximal to the conduit. In one embodiment, the ion depletion zone comprises at least a portion of the interface between the droplet and the conduit.

In one embodiment, the ion depletion zone or the area proximal to the conduit is an area within the droplet that is between 0-2 μm from the conduit. In one embodiment, the ion depletion zone or the area proximal to the conduit is an area within the droplet that is between 0-25 μm from the conduit. In one embodiment, the ion depletion zone or the area proximal to the conduit is an area within the droplet that is between 0-50 μm from the conduit. In one embodiment, the ion depletion zone or the area proximal to the conduit is an area within the droplet that is between 0-100 μm from the conduit. In one embodiment, the ion depletion zone or the area proximal to the conduit is an area within the droplet that is between 0-200 μm or 0-500 μm from the conduit. In one embodiment, the ion depletion zone or the area proximal to the conduit is an area within the droplet that is between 0-1000 μm from the conduit. In one embodiment, the phrase "ions are confined to a region within said droplet that is distant from said conduit" describes the region outside the ion-depletion zone. In one embodiment, the term "distant" reflects an area in the droplet that the distance between it and the conduit is at least the length of the ion-depletion zone. In one embodiment, the ion-depletion zone is an area around the conduit from which ions are depleted, and the ions are depleted to areas more distant from the conduit. In one embodiment, the area to which the ions are confined is an area that does not comprise the ion depletion zone. In one embodiment, the ion-depletion zone and the area to which the ions are confined are complementary.

In one embodiment, concentrating means "increasing the concentration of". In one embodiment, concentrating means that the number of concentrated species for a given volume unit is increased as compared to the number of concentrated species for a given volume unit before the concentration event had occurred. In one embodiment, depleting ions from the ion-depletion zone is equivalent to removing at least some of the ions from this area.

In one embodiment, a "ground", "grounded" or "electrically grounded" are terms used to describe the relative voltage applied to one side of the microchannels, to the reservoir, to one side of the conduits, or the relative voltage applied to regions or electrodes used in methods of this invention. In one embodiment, ground is the reference point in an electrical circuit from which other voltages are measured, a common return path for electric current (earth return or ground return), or a direct physical connection to the Earth. For measurement purposes, the earth or ground serves as a constant potential reference against which other potentials can be measured. In one embodiment, an electrical ground system serves as an adequate zero-voltage reference level.

In one embodiment, an external gate voltage is a voltage applied external to the microchannel or conduit of the invention, and not directly to the liquid carrying the charged species. In one embodiment, "gate" means that the application of such voltage can gate the liquid flow, by causing ions to move or to stop moving in a certain direction. In one embodiment, "gate" or "gating" means switching the direction of the flow, or switching the direction of migrating ions. In one embodiment, gating can stop flow. In one embodiment, gate voltage influences charged species by inducing an electric field. The electric field induced by the gate voltage may cause the accumulation, migration, depletion or a combination thereof of the charged species in or away from defined areas in the microfluidic channels.

In one embodiment, devices used in methods of this invention are made by lithography and etching processes. In one embodiment lithography and etching processes are the conventional processes used in the semiconductor fabrication industry. In one embodiment, lithography can be UV or optical lithography, electron-beam lithography, X-ray lithography, or a combination thereof. In one embodiment, etching can be dry or wet. In one embodiment, deposition processes are involved with methods of making devices of this invention. In one embodiment, stamping, molding, embossing, self-assembly, chemical vapor deposition, masking, nano-contact printing, dip-pen lithography and similar techniques can be used to make devices of this invention.

In one embodiment, methods of this invention are used for diminishing the concentration of ions in a solution. In one embodiment, diminishing the concentration of ions in a solution comprises the reduction in the number of ions in a certain volume of a solution. In one embodiment, this certain volume is part of the droplet. In one embodiment, diminishing the concentration of ions to in a solution comprises reducing the electrolyte strength of the solution.

In some embodiments, the devices of this invention comprise a conduit connecting between microchannels. In some embodiments, the term "conduit" may refer to a channel, a connector, a wire, a linkage, a solution-filled capillary, a porous material filled with fluid, an electrically conducting or semiconducting material. In one embodiment, a conduit is attached directly to the microchannels, or in one embodiment, via an adaptor, a filter, a junction or any other desired material, as will be appreciated by the skilled artisan. In some embodiments, the conduit is a junction between a sample microchannel and a buffer microchannel. In some embodiments, the conduit is a junction between a droplet and a buffer microchannel or reservoir. In some embodiments, flow is induced in the conduit. In one embodiment, ion flow is permitted through the conduit. It is to be understood that any structuring of the device to accommodate a conduit is what is to be understood as encompassed by the phrase "a conduit linked to said droplet and to said buffer microchannel or reservoir", and is part of the present invention.

In one embodiment, a conduit is a nanochannel. According to this aspect and in one embodiment, the conduit has at least one dimension ranging between 1 nanometer (nm) and 1000 nanometers (nm). In one embodiment, the conduit comprising a polymer-based permselective material. In one embodiment, the polymer-based permselective material comprising Nafion. In one embodiment, the polymer-based permselective material comprising a cation-selective or an anion-selective material. In one embodiment, the conduit comprising an electrical junction that is preferentially conductive to positive ions or to negative ions.

In one embodiment, the buffer comprises a buffer solution. In one embodiment, a buffer solution is a solution that resists change in hydronium ion ($H^+$) and in hydroxide ion ($OH^-$) concentration. Therefore, a buffer solution resists a pH change. The buffer solution can resist a pH change upon addition of small amounts of acid or base, or upon dilution. Buffer solutions consist of a weak acid and its conjugate base or a weak base and its conjugate acid. In one embodiment, the buffer solution comprises a phosphate buffer. In one embodiment, the buffer solution comprises an acetate buffer, Tris buffer, PIPES or HEPES buffers.

In one embodiment, the droplet is exposed to the environment. In one embodiment, the droplet is in contact with an edge of the concentration unit and is in contact with the fluids inside the sample microchannels and/or with the fluids inside the conduit. In one embodiment, the contact between the droplet and the environment enables the transfer of the droplet or portions of it to a different substrate or to a container. In another embodiment, the drop may be transferred to the concentration unit from a different substrate, container, tip, syringe or vessel for the purpose of concentrating species in the drop.

In one embodiment, the end of the first sample microchannel and the end of the second sample microchannel reach the edge of the concentration unit. In one embodiment, liquid within the sample microchannels is in contact with the environment at the ends of the sample microchannels. In one embodiment, when liquid is introduced to the first sample microchannel and reaches the open end of it, the liquid emerges out of the sample microchannel and forms a drop on the outside of the concentration unit. In one embodiment, when the drop is large enough, it becomes in contact with the open end of the second sample microchannel and with the liquid content of the second sample microchannel. In one embodiment, a continuous liquid system comprising the liquid (solution) within the first microchannel, the liquid within the droplet and the liquid within the second microchannel is formed. In one embodiment, the liquid within the conduit is also in contact with the liquid (or solution) of the droplet.

In one embodiment, the droplet can be formed on the surface or edge of the concentration unit by introducing it externally from a syringe, a tip, a dispenser, from another substrate, a tube, a pipette or a needle.

In one embodiment, exposed to the environment means in contact with the environment. In one embodiment, the environment is the surroundings, the atmosphere, or a region that is external to the concentration unit. In one embodiment, environmental conditions can be controlled. In one embodiment, controlled environmental conditions comprise pressure and/or temperature controlled conditions. In one embodiment, gas composition of the environment is controlled. In one embodiment, pressure of the environment is not equal to one atmosphere. In one embodiment, the temperature is 25 degrees Celsius and in another embodiment, 20 degrees Celsius. In one embodiment the pressure is controlled by placing the concentration unit and its surrounding in a chamber. In one embodiment, the chamber can be pumped to a pressure lower than one atmosphere or maintained under pressure that is higher than one atmosphere. In one embodiment, thermostats may be used to control the temperature of the chamber, the concentration unit, the environment or a combination thereof. In one embodiment, the environment comprises air. In one embodiment, the environment comprises $CO_2$, Ar, $N_2$, He, $O_2$, $H_2O$ or a combination thereof. In one embodiment, the environment may contain water molecules. In one embodiment, the environment may comprise any degree of humidity. In one embodiment, water in the environment reaches their due point. In one embodiment, the humidity of the environment is 100%. In one embodiment, the humidity of the environment ranges between 30% and 70%. In one embodiment, the humidity of the environment ranges between 1% and 50%. In one embodiment, the humidity of the environment ranges between 75% and 100%. In one embodiment, the humidity of the environment ranges between 25% and 50%. In one embodiment, the humidity of the environment ranges between 85% and 97%.

In one embodiment, an electrical junction is any junction that can pass an electrical signal or a junction between two or more points to which voltage can be applied, or a junction that enables an electrical signal from one side to affect the electrical state of another side of the junction. In one embodiment, an electrical junction may connect two or more wires or channels or areas such as an area of a droplet, wherein at least two of the wires/channels/areas have non-zero electrical properties such as electric field, voltage, current, charge accumulation etc. In one embodiment, devices of this invention comprises electrical junction that are preferentially conductive to either positive or negative ions. In one embodiment, the electrical junctions can be made of any porous material. In one embodiment the porous material can be organic and in another embodiment inorganic. In one embodiment, an inorganic material may comprise alumina, silica or both. In one embodiment, the porous material comprises particles. In one embodiment, the organic material comprises polymers. In one embodiment, the porous material comprises di- or tri-block copolymers.

In one embodiment, proximal means "in contact with". In one embodiment proximal means separated by nanometers, by micrometers or by millimeters. In one embodiment, proximal may mean close, nearby, adjacent, neighboring, local with respect to or in close proximity to.

II. DIMENSIONS AND VALUES

In one embodiment, a device of this invention may comprise a plurality of channels, including a plurality of microchannels, or a plurality of conduits, or a combination thereof. In one embodiment, the phrase "a plurality of channels" refers to more than two channels, or, in another embodiment, more than 5, or, in other embodiments, more than 10, 96, 100, 384, 1,000, 1,536, 10,000, 100,000 or 1,000,000 channels.

In one embodiment, the width of a microchannel is between 1-100 µm, or in another embodiment, between 1 and 15 µm, or in another embodiment, between 20 and 50 µm, or in another embodiment, between 25 and 75 µm, or in another embodiment, between 50 and 100 µm. In one embodiment, the width of the microchannel is between 1-5 µm, or in another embodiment, between 10 and 20 µm, or in another embodiment, between 0.5 and 10 µm, or in another embodiment, between 10 and 99 µm, or in another embodiment, between 75 and 100 µm.

In one embodiment, the depth of a microchannel is between 0.5-50 µm, or in another embodiment, between 0.5 and 5 µm, or in another embodiment, between 5 and 15 µm, or in another embodiment, between 10 and 25 µm, or in another embodiment, between 15 and 50 µm. In one embodiment, the depth of a microchannel is between 0.5-1.5 µm, or in another embodiment, between 1 and 9 µm, or in another embodiment, between 10 and 20 µm, or in another embodiment, between 10 and 50 µm, or in another embodiment, between 15 and 100 µm.

In one embodiment, the length of the microchannel is between 10 µm and 100 µm. In one embodiment, the length of the microchannel is between 10 µm and 100 µm.

In one embodiment, the length of the microchannel is between 10 µm and 100 µm. In one embodiment, the length of the microchannel is between 50 µm and 200 µm. In one embodiment, the length of the microchannel is between 100 µm and 1000 µm. In one embodiment, the length of the microchannel is between 100 µm and 5000 µm. In one embodiment, the length of the microchannel is between 1000 µm and 10000 µm. In one embodiment, the length of the microchannel is between 100 µm and 500 µm. In one embodiment, the length of the microchannel is between 20 µm and 75 µm.

In another embodiment, the width of a conduit is between 1 µm-50 µm, or in another embodiment, between 1 and 15 µm, or in another embodiment, between 10 and 25 µm, or in another embodiment, between 15 and 40 µm, or in another embodiment, between 25 and 50 µm. In another embodiment, the width of the conduit is between 1 µm-10 µm, or in another embodiment, between 0.1 and 1 µm, or in another embodiment, between 0.5 and 5 µm, or in another embodiment, between 0.01 and 0.1 µm, or in another embodiment, between 25 and 99 µm.

In another embodiment, the depth of a conduit is between 20-100 nanometers, or in another embodiment, between 20 and 50 nanometers, or in another embodiment, between 20 and 75 nanometers, or in another embodiment, between 30 and 75 nanometers or in another embodiment, between 50 and 100 nanometers. In another embodiment, the depth of the conduit is between 1-5 µm, or in another embodiment, between 0.1 and 1 µm, or in another embodiment, between 0.01 and 0.1 µm, or in another embodiment, between 10 and 75 µm or in another embodiment, between 25 and 100 µm.

In one embodiment, the length of the conduit is between 10 µm and 100 µm. In one embodiment, the length of the conduit is between 1 µm and 10 µm. In one embodiment, the length of the conduit is between 10 µm and 50 µm. In one embodiment, the length of the conduit is between 100 µm and 1000 µm. In one embodiment, the length of the conduit is between 50 µm and 500 µm. In one embodiment, the length of the conduit is between 100 µm and 500 µm. In one embodiment, the length of the conduit is between 20 µm and 75 µm.

In one embodiment, the device comprises multiple sample microchannels, multiple buffer microchannels, multiple reservoirs, multiple conduits or a combination thereof wherein the multiple entities are arranged in an array or with a particular geometry.

In one embodiment, the conduits are oriented in an angle that is different from 90 degrees with respect to the microchannels. In one embodiment, at least one of the conduits and at least one of the microchannels or a combination thereof are linear. In another embodiment, at least one of the conduits, at least one of the microchannels or a portion or a combination thereof are curved. In one embodiment, multiple channel arrays are placed one on top of the other in a device. In one embodiment, such design is referred to as a 3-D design. In one embodiment, the microfluidic device comprising arrays of channels comprises a three-dimensional (3-D) array structure, and in another embodiment, the microfluidic device comprising arrays of channels comprises a two-dimensional (2-D) structure. In one embodiment, two-dimensional (2-D) structure is a structure wherein the majority or all of the channels are arranged in one plane. In one embodiment, two-dimensional (2-D) structure is a structure wherein the majority or all of the channels, or the majority or all of the concentration units are arranged in parallel. In one embodiment, two-dimensional structure is a structure wherein the majority or all of the channels are constructed on or in the same surface. In one embodiment, three-dimensional (3-D) structure is obtained by placing several substrates, several surfaces, several concentration-units or several concentration unit arrays or several two-dimensional devices one on top of the other. In another embodiment, the three-dimensional (3-D) structure is constructed on or in one piece of substrate by e.g. lithography, etching and deposition methods.

In one embodiment, the number of arrays in a device is 1. In one embodiment, the number of arrays in a device is 1-10. In one embodiment, the number of arrays in a device is 10-100. In one embodiment, the number of arrays in a device is 10-1000. In one embodiment, the number of arrays in a device is 1-50. In one embodiment, the number of arrays in a device is 50-100. In one embodiment, the number of arrays in a device is 1000-10000. In one embodiment, the number of arrays in a device is 10000-1000000.

In one embodiment, the device length, width, height or a combination thereof ranges between 10 cm-30 cm. In one embodiment, the device length, width, height or a combination thereof ranges between 1 cm-10 cm. In one embodiment, the device length, width, height or a combination thereof ranges between 25 cm-50 cm. In one embodiment, the device length, width, height or a combination thereof ranges between 50 cm-100 cm. In one embodiment, the device length, width, height or a combination thereof ranges between 0.1 cm-1 cm. In one embodiment, the device length, width, height or a combination thereof ranges between 1 cm-5 cm. In one embodiment, the device length, width, height or a combination thereof ranges between 0.1 mm-1 mm. In one embodiment, the device length, width, height or a combination thereof ranges between 10 μm-100 μm. In one embodiment, the device length, width, height or a combination thereof ranges between 1 μm-10 μm. In one embodiment, the device length, width, height or a combination thereof ranges between 0.1 μm-1 μm. In one embodiment, the device length, width, height or a combination thereof ranges between 10 nm-100 nm.

III. EMBODIMENTS OF DEVICE DESCRIPTION AND METHODS OF OPERATION

In one embodiment, the device used in embodiments of this invention is constructed as diagrammed in FIG. 1. The first sample microchannel (channel 1) is the channel through which a sample comprising charged species can be made to pass. The first sample microchannel (channel 1) has a first side which is the left side of the sample microchannel shown in FIG. 1. The first sample microchannel (channel 1) has a second side which is the right side of the sample microchannel shown in FIG. 1. The first side (left) of the first sample microchannel is connected to at least one sample reservoir. In one embodiment, the sample reservoir is connected to the sample microchannel by means of a conduit, which may have the dimensions of the microchannel, or may have different dimensions. In one embodiment, the sample reservoir is capable of releasing a fluid or liquid comprising a species of interest or charged species into the first sample microchannel from the first side. In one embodiment, fluid or liquid entering the first sample microchannel has an initial flow direction from the left to the right side of the microchannel shown in FIG. 1.

In one embodiment, at least one buffer microchannel or reservoir ("ground channel") is placed in the vicinity or proximal to the first and the second sample microchannels. In one embodiment, the buffer microchannel or reservoir is filled with buffer.

In one embodiment, at least one conduit (nanojunction) is linked to the environment and to the area between the first and the second sample microchannels (channels 1 and 2) and is also linked to the at least one buffer microchannel or reservoir (ground channel).

In one embodiment, a drop is present at an area comprising an edge of the device, such that the droplet liquid or solution is in contact with the liquid or solution in the first and in the second sample microchannels and with the conduit. At least portions of the droplet are exposed to the environment as shown in FIG. 1(a). The droplet can form by introducing a liquid or solution from the first sample microchannel. Alternately, the droplet can be formed using an extra syringe or tip, or by introducing liquid from the second sample microchannel. In one embodiment, the droplet can be formed by introducing liquid from both the first and the second microchannels. In one embodiment, a drop that was formed by introducing liquid from the first and/or second microchannels can be enlarged by introducing liquid from an extra syringe or tip that are not an integral part of the concentration unit.

In one embodiment, the conduit is made of flat nanofluidic filters filled with buffer solution. In one embodiment, the nanofluidic filters serve as an ion-selective membrane allowing selected ions to pass from one area to another within the conduit. In one embodiment, movement or migration of ions within the conduit is a result of an electric field induced in the conduit. In one embodiment, the movement or migration of ions within the conduit, changes or controls the magnitude of an electric field in the vicinity of the conduit. In one embodiment, movement of fluid in the conduit is by capillary forces.

In one embodiment, when an electric field is induced in the conduit, it affects a region in the droplet that is proximal to the conduit. In one embodiment, such electric field generates a depletion zone in the droplet that is proximal to the conduit. In one embodiment, the depletion zone is a region depleted of charged species. In one embodiment, charged species are pushed away from the ion depletion zone. In one embodiment, the effect of the electric field in the conduit is to reduce the concentration of ions or charged species in the area proximal to the conduit, by forcing the charged species away from the conduit area. In one embodiment, the ion depletion zone shown in FIG. 1 (white area of the droplet), represent the region in the droplet that has a lower concentration of charged species as compared to the dark region on the left side of the droplet in which charged species or ions accumulate. This process is a result of the electric field induced in the conduit. In one embodiment, the ion depletion zone or the desalted zone has no charged species. In one embodiment, the ion depletion zone has a low concentration of charged species. In one embodiment, the ion depletion zone has charged species concentration that is lower than the charged species concentration in the non-depleted area or areas of the droplet and of the sample microchannel.

In one embodiment, this invention comprise inducing a second electric field in the conduit, whereby charged species depletion occurs in a region proximal to said conduit within the droplet and whereby the charged species are confined to another region within said droplet. According to this aspect and in one embodiment, the region proximal to the conduit may be represented by the white region on top of the conduit in FIG. 1a. The charged species are depleted from this region. The "another region" to which the charged species are confined may be represented by the dark area to the top and to the left of the conduit (within the droplet and within a portion of channel 1), wherein the charged species are concentrated.

In one embodiment, the electric field induced in the conduit is denoted $E_N$ as shown in FIG. 1.

In one embodiment, induction of the electric field $E_N$ in the conduit, induces the concentration of the charged species of interest within one region of the droplet, while depleting it from another region of the droplet.

In one embodiment, fluid flow in the microchannels from the first side (left in FIG. 1) to the second side (right side in FIG. 1) is pressure driven. In another embodiment, fluid flow from the first to the second side of the sample microchannel is induced by an electric field. In one embodiment, such electric field induced in the microchannels is denoted $E_T$. In one embodiment, $E_T$ is induced as a result of a potential difference between the first and the second sample microchannels. In one embodiment, $E_T$ is induced in the droplet as denoted in FIG. 1. In one embodiment, the potential difference is achieved by applying a higher voltage to the first (left most) side of the first sample microchannel and a lower voltage to the second (right most) side of the second sample microchannel. In one embodiment, the higher voltage is denoted $V_H$ and the lower voltage is denoted $V_L$. In one embodiment, $V_H$ is 400 V and $V_L$ is 350 V.

In one embodiment, the flow is a result of pressure and/or electric field applied to the sample microchannels.

In one embodiment, the generation of the depletion region by $E_N$, causes and/or accelerates fluid flow from the left side to the right side or from the first to the second sample microchannels. In one embodiment, $E_N$ can be used to accelerate the fluid flow from the right side to the left side or from the second side to the first side of the sample microchannels. In one embodiment, $E_N$ depend on its magnitude can cause a flow to stop or can cause reversal or switching of flow direction. In one embodiment, all such flow directions and rates can be induced inside the droplet or portions thereof.

In one embodiment, a method of this invention generates a depletion region and an accelerated liquid flow within the droplet efficiently because of a nonlinear electroosmotic flow (much stronger than normal electroosmotic flow) generated in the sample microchannels, which draws fluid into the first microchannel from a sample reservoir or inlet with high flow speed, and because an energy barrier for anionic molecules is generated by the induced space charge layer (the ion depletion zone) in the microchannel, at regions of apposition to the conduit(s).

In one embodiment, the two separate electric fields $E_N$ and $E_T$ are applied to the device, as shown in FIG. 1. The field in the nanofluidic channel ($E_N$) generates an ion-depletion region (colored white area within droplet in FIG. 1) and an extended space charge layer that traps charged species. The tangential field in the microfluidic channel ($E_T$), generates electroosmotic flow, which draws charged species into the trapped region (colored with dark within the droplet and within the end of the first sample microchannel in FIG. 1) from the reservoir.

In one embodiment, the space charge region is further stabilized by manipulating buffer conditions in the devices of the invention. In one embodiment, the device comprises one or two buffer microchannels, or a reservoir, connected by a conduit to the sample microchannel. According to this embodiment, over a course of time, ion depletion in the droplet leads to ion enrichment in the buffer microchannel or reservoir, such that the buffer concentration in the buffer channel or reservoir increases with prolonged conduction of a species separation process or of any other prolonged device operation. By providing a lower concentration buffer, at prescribed time periods, in one embodiment, or continually, in another embodiment, by electroosmosis, or in another embodiment, by pressure driven flow, or by any other means in the buffer microchannel, this effect is mitigated, according to this embodiment.

In one embodiment, the electric field induced in the conduit is a result of the voltages applied to the sample and buffer microchannels. In one embodiment, the voltages applied to the sample microchannel are VH=400 V and VL=350V. The buffer microchannel or reservoir is grounded as shown in FIG. 1. If the buffer reservoir is in the form of a ground channel as shown in to FIG. 1, the channel can be grounded on both ends. The voltage difference between the conduit side that is linked to the droplet and the conduit side that is linked to the buffer microchannel or reservoir is the result of the higher voltages applied to the sample microchannels with respect to the buffer microchannel or reservoir. This voltage difference on the conduit generates the electric field in the conduit that in turn, generates the ion-depletion zone in the droplet.

In one embodiment, the flow in the microchannels and into and out of the droplet may be pressure-driven, and may be accomplished by any means well known to one skilled in the art. In another embodiment, the flow may be a hybrid of pressure-driven and electro osmotic or electrokinetic flow.

In one embodiment, the phrases "pressure-driven flow" refers to flow that is driven by a pressure source external to the channel segment through which such flow is driven, as contrasted to flow that is generated through the channel segment in question by the application of an electric field through that channel segment, which is referred to herein, in one embodiment, as "electrokinetically driven flow."

Examples of pressure sources include negative and positive pressure sources or pumps external to the channel segment in question, including electrokinetic pressure pumps, e.g., pumps that generate pressure by electrokinetically driven flow in a pumping channel that is separate from the channel segment in question, provided such pumps are external to the channel segment in question (see, U.S. Pat. Nos. 6,012,902 and 6,171,067, incorporated herein by reference in their entirety).

In one embodiment, the term "electrokinetic flow" refers to the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, when referred to in terms of electrokinetic flow, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

In one embodiment, reference to the term "liquid flow" may encompass any or all of the characteristics of flow of fluid or other material through a passage, conduit, or channel or across to a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

In one embodiment, hybrid flow may comprise pressure-based relay of the liquid sample into the channel network, followed by electrokinetic movement of materials, or in another embodiment, electrokinetic movement of the liquid followed by pressure-driven flow.

In one embodiment, pressure driven flow may be induced by a syringe, a pump and/or any suction mechanism. The rate of the pressure driven flow may be controlled. The flow can be continuous or performed in a stepwise manner. The flow can be used to generate the droplet and to control the droplet size.

In one embodiment, the electric field may be induced in the respective channels by applying voltage from a voltage supply to the device. In one embodiment voltage is applied by way of the placement of at least one pair of electrodes capable of applying an electric field across at least some of the channels in at least one direction. Electrode metal contacts can be integrated using standard fabrication technology to be in contact with at least one sample or buffer microchannel, or in another embodiment, at least one conduit, or in another embodiment, a combination thereof, and oriented as such, to establish a directional electric field. Alternated direction voltages, uni-directional voltages or both types of voltages can be applied to obtain the desired electric fields. The electrodes can be made of almost any metal, and in one embodiment, comprise thin Al/Au metal layers deposited on defined line paths. In one embodiment, at least one end of one electrode is in contact with buffer solution in the reservoir.

In one embodiment, portions of the electrodes are made of any conducting material. In one embodiment, electrodes are made of metals, doped semiconductors, or conducting organic materials. In one embodiment, electrodes are made of a combination of materials. In one embodiment, electrodes are made of gold, carbon, glassy carbon, pyrolytic carbon, Al, Cu, Pd, Pt, Ag, or a combination thereof. In one embodiment the electrode comprises mercury. In one embodiment, the electrodes comprise solutions of salts. In one embodiment at least one electrode is a silver/silver chloride electrode (Ag/AgCl). In one embodiment at least one electrode is a saturated calomel electrode (SCE), a normal hydrogen electrode (NHE) also known as a standard hydrogen electrode (SHE), a copper-copper(II) sulfate electrode or a combination thereof. In one embodiment, at least one electrode is a microelectrode or an ultramicroelectrode. In one embodiment, a plurality of microelectrodes is used. In one embodiment, at least one electrode is fabricated as part of the substrate.

According to this aspect and in one embodiment, at least one electrode is constructed in, on, parallel to, perpendicular to the substrate from which the device is made. In one embodiment, the device is sealed or covered by a flat or curved surface. In one embodiment, at least one electrode is embedded in or fabricated into or onto the cover or sealed material such that at least a portion of the electrode interfaces with the sample or buffer microchannels or with the conduit/s or with a combination thereof.

In another embodiment, methods of this invention utilize at least two pairs of electrodes. In one embodiment, additional electrical contacts can be used to independently modulate the direction and amplitudes of the electric fields in order to orient the space charge layer, or to move macromolecules at desired speed or direction or a combination thereof.

In one embodiment, the voltage applied to any of the electrodes is between 50 mV and 500V. In one embodiment, the voltage applied to any of the electrodes is between 50 V and 500 V. In one embodiment, the voltage applied to any of the electrodes is between 10 mV and 100 V. In one embodiment, the voltage applied to any of the electrodes is between 1 V and 30 V. In one embodiment, the voltage applied to any of the electrodes is between 10 V and 40 V. In one embodiment, at least one electrode is not connected and referred to as a "floating" electrode. In one embodiment, at least one electrode is grounded. In one embodiment, instead of having a "floating" electrode that is not connected to an electrical circuit, the position in the microchannel that needs to be "floated" is not connected to an electrode.

In one embodiment, the voltage supply may be any electrical source, which may be used to provide the desired voltage. The electrical source may be any source of electricity capable of generating the desired voltage. For example, the electrical source may be a piezoelectrical source, a battery, or a device powered by household current. In one embodiment, a piezoelectrical discharge from a gas igniter may be used. In one embodiment, conventional power supply apparatuses are employed.

In one embodiment, the electrokinetic trapping of charged species in the device and sample collection can occur over a course of minutes, or in another embodiment, can be maintained for several hours. In one embodiment, depletion of a species from one region and its accumulation in another region over a course of time results in species concentration factors as high as $10^6$-$10^8$, and in another embodiment, may be even higher, upon optimization of the conditions employed during the concentration, such as by modifying the interface between the microchannel and conduit, voltage applied, additional gate voltages applied, salt concentration of the liquid, pH of the liquid, number, size and geometry of the conduits, geometry of the sample microchannel or combination thereof. In another embodiment, concentration of species is by factors ranging between $10^1$ and $10^6$.

In another embodiment, methods of this invention further comprises at least one waste reservoir in fluid communication with the second sample microchannel or microchannels, the buffer microchannel or microchannels, or the conduit or conduits or the area of or proximal to the droplet of the microfluidic device. In one embodiment, the waste reservoir is capable of receiving a fluid.

In one embodiment, instead of or in addition to the waste reservoir, a collection reservoir is connected to the sample microchannel in order to collect species of interest, ions, desalted solution, pure liquid or a combination thereof. In one embodiment, the collection reservoir is connected to the second side of the second sample microchannel and in another embodiment the collection reservoir is connected to the first side of the first sample microchannel. According to this aspect of the invention and in one embodiment, connecting the collection reservoir to the first side of the first sample microchannel is advantageous in cases where liquid flow is reversed or switched or stopped, and species or liquids can be collected at the first side of the sample microchannel.

In another embodiment, the device, or in another embodiment, the microchannel or microchannels are capable of being imaged. Imaging of the device, or parts thereof, may be accomplished by presenting it to a suitable apparatus for the collection of emitted signals, such as, in some embodiments, optical elements for the collection of light from the microchannels.

In one embodiment, the device may be disposable, and in another embodiment, may be individually packaged, and in another embodiment, have a sample loading capacity of 1-50,000 individual fluid samples. In one embodiment, the device can be encased in a suitable housing, such as plastic, to provide a convenient and commercially-ready cartridge or cassette. In one embodiment, the device of this invention will have suitable features on or in the housing for inserting, guiding, and aligning the device, such that, for example, a sample loading compartment is aligned with a reservoir in another device, which is to be coupled to the device of this invention. For example, the device of this invention may be equipped with insertion slots, tracks, or a combination thereof, or other adaptations for automation of the concentration process via a device of this invention.

In one embodiment, the device is part of a kit. In one embodiment, the device is part of an assay kit. In one embodiment, the device is part of a kit for analysis of biological species. In one embodiment, the device is part of a kit that performs separation, isolation, concentration, qualitative analysis, quantitative analysis, microsynthesis or a combination thereof.

The device may be so adapted, in one embodiment, for high throughput manipulation of multiple samples, such as will be useful in concentration, purification, dilution and analysis applications, as will be appreciated by one skilled in the art.

In one embodiment of the present invention, the device of this invention is part of a larger system, which includes an apparatus to excite species inside the channels and detect and collect the resulting signals. In one embodiment, a laser beam may be focused upon the sample species concentration region, using a focusing lens, in another embodiment. The generated light signal from the species inside the microchannels may be collected by focusing/collection lens, and, in another embodiment, reflected off a dichroic mirror/band pass filter into optical path, which may, in another embodiment, be fed into a CCD (charge coupled device) camera.

In another embodiment, an exciting light source could be passed through a dichroic mirror/band pass filter box and focusing/collecting scheme from the top of the device of this invention. Various optical components and devices can also be used in the system to detect optical signals, such as digital cameras, PMTs (photomultiplier tubes), and APDs (Avalanche photodiodes).

In another embodiment, the system may further include a data processor. In one embodiment, the data processor can be used to process the signals from a CCD, to a digital image of the concentrated species onto a display. In one embodiment, the data processor can also analyze the digital image to provide characterization information, such as size statistics, histograms, karyotypes, mapping, diagnostic information and display the information in suitable form for data readout.

In one embodiment, the liquid comprises charged or uncharged species or a combination thereof. In one embodiment, the liquid comprises, ions, complex ions, neutral molecules, charged molecules, cluster of atoms, clusters of particles, beads, nanospheres, biological molecules or fragments thereof, amino acids, peptides, proteins, protein complexes, enzymes, DNA, vectors, RNA, nucleotides, lipids, phospholipids, cholesterol, mono-, di-, oligo-, or poly-saccharides, organic or inorganic salts, NaCl, KCl, KI, NaI, Calcium containing salts, $H^+$ ions, ammonium ions, nitrates, sulfates, acids bases, strong electrolytes, weak electrolytes, or non electrolytes.

In certain embodiments of the present invention, the methods may utilize an apparatus for transporting solutions or pure liquids from the microchannels and/or from the droplet into the waste reservoirs.

In one embodiment, this invention provides an array architecture that is capable of being scaled to at least 10,000 devices, suitable for real-world applications.

In one embodiment, fluid speed, concentration and pumping efficiency may be determined by using labeled proteins or polypeptides or fluorescent markers, introduced into the microchannels, droplet or reservoirs in known ratios and detecting the concentration of labeled protein or polypeptides, or fluorescent markers using any detection technique know in the art such as UV/Vis or IR spectroscopy or fluorescence. Signal intensity can be determined as a function of time, over background noise.

In one embodiment, devices used in the methods of this invention may be under controlled physicochemical parameters, which may comprise temperature, pressure, pH, solution concentration and contents, environment chemical composition or a combination thereof.

In one embodiment, the conduit is made of a perm selective material. In one embodiment, the conduit is filled with fluid. In one embodiment, the conduit is permeable to one type of ions and is not permeable to another type of ions. In one embodiment, the conduit is a structure permeable to $H^+$ ions. In one embodiment, the conduit may be made of a charged gel or random nanoporous material, wherein charged group are embedded in the nanoporous material. In one embodiment, according to this aspect of the invention, the charged gel or nanoporous material may have a similar pore size. According to this aspect of the invention, a space charge layer may be generated in the charged gel or random nanoporous material, similar to that formed in the conduit as described and exemplified herein, wherein an electric field is induced in the nanoporous charged gel or charged material, similar to that induced in the conduit.

In one embodiment, this invention provides a microfluidic pump comprising a device of this invention, which in one embodiment has a liquid flow speed of between 10 µm/sec and 10 mm/sec.

In one embodiment, within the thin nanofluidic channel, perm-selective portion of ion currents, caused by the counter ions within the Debye layer cannot be ignored, compared with the total ion current through the conduit, therefore, more counter ions (from the Debye layer) than co-ions migrate across the conduit when an electric field is applied resulting in a net transfer of charges (counter ions) from the anodic side to the cathodic side, and a concentration polarization effect. According to this aspect of the invention, ion depletion near the nanofluidic channel thickens the Debye layer, causing its overlap more significantly in the nanofluidic channel, speeding up the concentration polarization effect, and above a certain threshold En value, results in electroosmosis with second order kinetics.

According to this aspect of the invention, counter ion depletion from the nanofluidic channel, and creation of an extended space charge layer in bulk solution within the sample microchannel prevents co-ion migration in this region. In one embodiment, controlling the electric fields ($E_N$ and $E_T$), to balance the two forces (anion repulsion from the space charge layer vs. nonlinear electroosmotic flow from the reservoir), stabilizes the interface, which is where anionic species of interest are trapped and collected, according to this aspect of the invention. In one embodiment, electric-field induced concentration mechanisms are described in patent application Ser. No. 11/338,885 fully incorporated herein by reference.

In one embodiment, the liquid is a solution. In another embodiment, the liquid is a suspension, which, in another embodiment is an organ homogenate, cell extract or blood sample. In one embodiment, the species of interest comprises proteins, polypeptides, nucleic acids, viral particles, or combinations thereof. In one embodiment, the species of interest is a protein, nucleic acid, virus or viral particle found in, or secreted from a cell, and in another embodiment, is found in very low quantities, such that it represents less than 10% of the protein extracted form a protein extract of the cell.

Conduits thinner than 50 nm demonstrate unique ion-perm-selectivity at moderate ionic strength, due to the fact that the Debye layer thickness is non-negligible compared with the channel thickness in these conduits. Often these phenomena are explained as Debye layer overlap, with the ratio between (equilibrium) Debye length and the channel dimension as the critical parameter. Typical ion behavior is such that the anodic side of the conduit is almost completely depleted from ionic species, while ion enrichment occurs in the cathodic side of the conduit, in some embodiments, attributable to the permselective nature of the conduits at low-ionic strength conditions, caused by the Debye layer overlap in the conduits. According to this aspect of the invention, due to this concentration gradient, preferential cation transport through the conduit is satisfied across the entire system, while maintaining net zero anion flux at the cathodic side.

According to this aspect of the invention, and in one embodiment, typically in the perm-selective membrane facing the bulk solution, there exist a diffusion layer outside of which convective mixing eliminates any concentration gradient, rendering the ion concentration comparable to that of bulk solution. In some embodiments, when the device operation is with a fixed diffusion length and increasing DC bias, the system responds by decreasing the local ion concentration on the anodic side of the membrane or the conduit. While it would be predicted that when this happens the system reaches a limiting current, above which no further increase in ion current is possible even with higher voltage applied to the system, surprisingly, it was found herein that significant over-limiting current can be observed in most perm-selective membranes, and in this case, the electrokinetic response may be amplified because of significantly lowered ion concentration near the conduit, therefore higher "local" zeta potential.

In some embodiments, the methods of this invention result in the acceleration of liquid flow in a microchannel and in a droplet. In one embodiment, the methods of this invention result in controlling liquid flow in a microchannel and in a droplet.

FIG. 2 is an embodiment of a method of the present invention wherein a species of charge in a liquid is concentrated and wherein part of the droplet is being transferred to another substrate. The detection of the concentrated species is done using fluorescence. The species of interest comprise the fluorescent marker FITC. Applied voltages are V1=400 V, V2=350 V and V3=V4=0 V. Initially (at t=0 sec) no fluorescence is detected in the droplet. The concentrated plug (area of concentrated species) is formed from the first sample microchannel side, channel 1 side (at t=5 sec), and then inside the droplet (t=10 sec). After 15 seconds (at t=15 sec), the fluorescence is concentrated at the left side of the droplet. The droplet size is increasing since the induced force of EOF is stronger than the surface tension. The bright shell in (t=10 sec) is due to reflection. FIG. 2(*b*) is an image demonstrating direct contact dispensing from PDMS to a MALDI sample plate. The Droplet stays on the surface of the PDMS connected to a microchannel at t=0 sec. Upper image of the droplet is a reflection on the MALDI sample plate. The MALDI plate moved downward to form a liquid bridge at t=3 sec. The plate moves upward and liquid bridge breaks, leaving a droplet on the plate surface at t=6 sec. FIG. 2(*c*) reflects the area of saturated brightness inside the droplet which reflects the area of highly concentrated species. It was first analyzed within half of the droplet (region (i)) and then to neglect the reflection near the edge, the inner part of the droplet (region (ii)) was analyzed. As time goes, the area of saturated brightness increases, confirming the concentration process inside the droplet.

In one embodiment, the methods of concentrating a species of interest may be useful in biosensor devices. In one embodiment, concentration of a minute quantity of a species of interest for detection is a critical element of a biosensor device. In one embodiment, such methods are particularly useful in detecting organisms in a latent or spore state, wherein detection of the organism is otherwise difficult.

In other embodiments, various applications of the methods of the present invention are possible without deviating from the present invention. For the method of concentrating a species in a liquid, for example, multiple microchannels may be so deposited such that droplet content is directed to a central reservoir, to which additional microchannels may be connected. According to this aspect, the fluid once within the reservoir may then be mixed, and in turn, be pumped through the second set of microchannels to another reservoir connected thereto, for further manipulation. It can be appreciated that the concentration method of the present invention works with various types of fluids including water and biological fluids.

By way of example, the concentrating methods of the present invention allow for high-throughput robotic assaying systems to directly interface with the devices of the present invention, and to concentrate a species of interest.

In one embodiment, the dark region containing the charged species, shown on the left side of the droplet as depicted in FIG. 1 is called the ion-concentration plug.

As shown in FIG. 3 an integrated system or an array of devices can be formed. FIG. 3(*a*) shows an embodiment of an integrated device for parallel dispensing. Multiple devices are stacked up into one big device with different samples on the bottom. This can be connected to a motorized-stage to dispense droplet on a target surface (possibly protein/DNA microarrays). This dispensing can be done either simultaneously or separately, depending on the motorized stage configuration. In FIG. 3(*b*), devices are shown bonded to a glass plate, where analysis can be done on-plate.

In some embodiments, the charged species concentration as a result of the methods/using the devices of this invention is appropriate for MALDI sample preparation and for MALDI detection.

In some embodiments, the concentrating methods/devices of this invention, or devices/methods for the isolation of a species of interest have a high flow rate even in the absence of additional mechanical pumping mechanisms, which in some embodiments, is superior to current electro-osmotic pumping devices. In some embodiments, the high flow rate is useful in high throughput sample preparation for micro-total analysis systems and for micro-synthesis.

Methods of this invention may employ various configurations of a device. Devices used in methods of this invention may have different features, different dimensions, different number of microchannels and conduits, different inlets and outlets and various sample, buffer, collection and waste reservoirs or containers.

In other embodiments, separation devices connected to or working with devices of this invention, which may interface with the droplet, or concentrated species or sample microchannels of this invention include, but are not limited to, micro high performance liquid chromatographic columns, for example, reverse-phase, ion-exchange, and affinity columns.

It is to be understood that the exact configuration of any systems, devices, etc. which are coupled to the droplets or to the concentrated species of the device are to be considered as part of this invention, and that the configuration may be varied, to suit a desired application. In one embodiment, a module for separation of concentrated peptides which is positioned in contact with the droplet or the droplet contents of the concentrating device comprises a separation medium and a capillary between the ends of which an electric field is applied. The transport of a separation medium in the capillary system and the injection of the sample to be tested (e.g., a sample band comprising peptides and/or partially digested polypeptides) into the separation medium can be carried out with the aid of pumps and valves, or in another embodiment, via electric fields applied to various points of the capillary.

In another embodiment, the method is utilized to detect said species of interest when said species is initially present in said liquid at a concentration, which is below a limit of detection.

IV. EMBODIMENTS OF METHODS OF THE INVENTION

In one embodiment, the method is used for analysis of a charged species. In one embodiment, the species that was concentrated in the droplet according to methods of this invention is conveniently transferred from the droplet to a measurement system without decreasing the concentration of the species. In one embodiment, such direct transfer can be done using a needle, a tip, a syringe, or substrate by bringing the needle, tip, syringe, or substrate into contact with the droplet and by retrieving it, until at least a portion of the droplet is transferred to the needle, tip, syringe, or substrate. This type of transfer is advantageous over in-channel delivery wherein the high concentration is lost while the sample flows in the channel through the device. Direct transfer of the concentrated species in a liquid from the droplet is faster and more efficient than collection by flow through channels.

In one embodiment, the solution containing the concentrated species is transferred to another device or to another system directly. In one embodiment, the solution containing the concentrated species is transferred to another device or to another system without the need to flow the solution. In one embodiment, the solution containing the concentrated species is transferred to another device or to another system without diluting it. In one embodiment, the solution containing the concentrated species is transferred to another device or to another system by dispensing the droplet (or portions thereof) containing the concentrated species. In one embodiment, the solution containing the concentrated species is transferred to another device or to another system by suction of the droplet (or portions thereof) containing the concentrated species. In one embodiment, the solution containing the concentrated species is being analyzed without transfer. According to this aspect and in one embodiment, an analysis system is constructed such that the contents of the droplet can be analyzed on the edge of the concentration unit. Such analysis systems may include but are not limited to spectrometers and imaging and microscopy instruments.

Because the droplet is exposed to the environment, analysis can take place without the need to transfer the species. Spectral analysis for example can be carried out by irradiating the droplet and detecting the change in radiation.

In one embodiment, the method is adapted for synthesis in the micron scale. In one embodiment, synthesis in the micron scale comprises synthesis using volumes in the micro-liter range. In one embodiment synthesis in the micron scale comprises reactors, bio-reactors, synthesis containers, and/or sample tubes, channels or conduits having at least one dimension ranging between 1 micrometer and 1000 micrometer. In one embodiment synthesis in the micron scale or microsynthesis is referred to small scale synthesis, synthesis wherein small amounts of reactants are used, and small amounts of products are being produced. In one embodiment, such synthesis is directed toward expensive materials, sensitive materials, rare materials, hazardous materials, high purity products, medicinal products, drugs, unstable materials or derivatives thereof.

In one embodiment, methods and devices of this invention are used in drug synthesis and in drug development. In one embodiment, synthesis intermediates are concentrated by methods of this invention before using it for further synthesis steps. In one embodiment, final products (drugs or other materials) are concentrated by methods of this invention before being used or before being stored and/or packaged. In one embodiment, starting materials for drug or for other material's synthesis are concentrated by methods of this invention before being used for synthesis. In one embodiment, concentration methods of this invention help in purification and in isolation of synthesized materials and/or drugs. In one embodiment, drugs concentrated by methods of this invention are used for therapeutics.

In one embodiment, the method is adapted for chemical or biological analysis. In one embodiment, methods of this invention provide fluid dilution and/or species concentration in a fluid that may aid in chemical and biological analysis.

In one embodiment, concentrating a charged species reduces the time needed for analysis. In one embodiment reducing the time also reduces the cost of the analysis. In one embodiment, concentrating a charged species of interest enables to carry out analysis of unstable or sensitive materials, materials that deteriorate or decompose after a certain period of time.

In one embodiment, the method is adapted for sampling or diagnosis.

In one embodiment, the method is adapted to implanted devices where injection of a solution into or out of the device is required. In one embodiment, such implanted device can be operated remotely. In one embodiment, such implanted device can be used for sampling of body fluids on a regular basis.

In one embodiment, an implanted device working according to methods of this invention may be used to release drugs in accurate doses and at precise times into a patient's blood stream or into a tissue.

In one embodiment, devices and methods of this invention could be used as a sample delivery system for DNA/protein microarrays, providing additional boost in the detection sensitivity and dynamic range. Devices and methods of this invention are amenable to massive parallelization and do not suffer from the technical difficulties of integrating microfluidic immunoassay systems, since the concentrated sample plugs are readily available in droplets for any surface-based assays.

In one embodiment, concentration processes of this invention exhibit concentration of species in a volume of liquid that is exposed to the environment. In one embodiment, this feature enables to use the concentrated species within the volume of liquid directly without the need to flow the concentrated species through a channel to a collection area. By running a liquid comprising a concentrated species in a channel, the concentration of the species decreases. This decrease in concentration and dilution of the species is eliminated in methods of this invention because the volume of liquid in which the concentrated species is present can be collected directly. The volume of liquid in which the concentrated species is present can be collected by dispensing it, or by transferring it upon contact to another substrate or to a container. The concentrated species can be collected directly using a syringe or a pipette, by suction, by applying positive or negative pressures, such that the volume of liquid in which the concentrated species of interest is present does not mix with other diluting volumes of liquid. Accordingly, the concentration of species does not decrease during transfer in one embodiment.

Various modes of carrying out the invention are contemplated as being within the scope of the following claims particularly pointing out and distinctly claiming the subject matter, which is regarded as the invention.

EXAMPLES

Materials and Methods

Device Fabrication:
PDMS was used to fabricate the preconcentrator (a concentration device of this invention) following a general PDMS chip fabrication process. As the first step, an SU8 photoresist pattern on silicon wafer was used as a master. The positive master mold contained microchannels. As the second step, PDMS was poured on the master mold. After curing in an oven at 65 degrees C. for 3 hours, the PDMS layer was peeled off from the master. For nanojunction fabrication, self-sealed method was utilized (S. J. Kim and J. Han, Anal.

Chem. 80, 3507-3511 (2008)). The polymeric nanojunction was created by infiltrating Nafion polymer solution between the gaps created by mechanical cutting on PDMS substrate which had a mold of microchannels. The PDMS can seal itself with the heterogeneous polymeric nanoporous material between PDMS/PDMS gap. Then the PDMS substrate was bonded with glass plate by plasma treatments.

Biomolecule and Reagent Preparation

A 1 mM solution of potassium phosphate dibasic solution (pH=8.4) was used as a main buffer solution and it contained 1 µg/ml of FITC (Sigma-Aldrich, St. Louis, Mo.) for fluorescent tracking.

Optical Detection Setup

Experiments were conducted on an inverted microscope (IX-71) with fluorescence excitation light source attached. A thermoelectrically cooled CCD camera (Cooke Co., Auburn Hill, Mich.) was used for fluorescence imaging. Sequences of images were analyzed by IPLab 3.6 (Scanalytics, Fairfax, Va.). A dc power supply (Keithley 236 source measure unit (SMU)) was used to apply electrical potential to each reservoir using a custom-made voltage divider. The built in 100 W mercury lamp was used as a light source, and a neutral density filter was used to reduce the light intensity and to increase the dynamic range of detection.

Example 1

High Performance Preconcentrator

As shown in FIG. 1($a$), two microchannels (channel 1 and channel 2) are open to the outside of the PDMS chip. Injecting sample liquid from either channel 1 or channel 2 can create droplet that can connect two channels. Ground channel, which buried inside the PDMS chip, is connected to the droplet through via nanojunction. Once DC was applied with depletion voltage conditions (V1=V2=V and V3=V4=0), CP was initiated and the ionic concentration in anodic side started to deplete (ion depletion zone) with the normal electric field (EN) through nanochannel. Then adjusting V2 lower than V1 (preconcentration voltage condition) gives tangential electric field (ET) through the droplet. With the application of the tangential electric field (ET), any charged species would accumulate and form a preconcentrated plug inside the droplet. The electric potential can be applied by the electrodes as shown in FIG. 1($b$). This preconcentration voltage condition can also maintain (or control) the size of the droplet. Since the droplet is formed at open environment, evaporation would make the size of droplet decrease. However, since the flow rate into/out of droplet can be maintained much higher than the evaporation rate, this voltage configuration can keep (or control) the size of droplet.

Successful concentration process was achieved with applied voltages of V1=400V, V2=350V and V3=V4=0V as shown in FIG. 2($a$). Initially no fluorescence is in the droplet (t=0 sec). The concentrated plug is formed from the channel 1 (t=5 sec), and then inside the droplet (t=10 sec). After 15 seconds, the fluorescence are concentrated at the left side of the droplet (t=15 sec). The droplet size is slightly increasing since the induced force of EOF is stronger than the surface tension. In this example, the droplet size slightly increases from 696 µm to 768 µm. The bright shell in the image of t=10 sec is due to reflection. In order to remove the reflection effect near the edge, the saturated fluorescent area of region (i) (the half of droplet) and region (ii) (the inner part of droplet) was measured as shown in FIG. 2($c$). The area is exponentially growing and shows excellent preconcentration efficiency.

Example 2

High Concentration Drop Dispenser

A microfluidic device is constructed. Due to its microscale size, the droplet on the PDMS chip has a hemispherical shape. With upper plate or objects touching the droplet, droplet changes itself into a liquid bridge. By moving the plate away, liquid bridge breaks apart into two droplets, splitting the samples into two (FIG. 2 ($b$)). In this method, concentrated sample transfers directly to the target plate without any driving force for transporting (external pressures or electric fields), restricting plug dispersion or electrodiffusion. Also, it can be easily integrated into a massively parallel sensor array (FIG. 3($a$)) since the sample droplets locate at the edge of the device.

In addition to this, the parallelization can be done even without dispensing process as shown in FIG. 3($b$). Microchannels in PDMS are bonded to large glass rather than PDMS itself so that the resulting droplets would be quarter spherical shape and directly react with molecules on the glass surface. Since glass surface is the most widely used surface for immunoassay or other chemical treatments, this method can be used for most of the processes where higher concentration is needed.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein.

Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An electrokinetic concentration device comprising:
   at least one concentration unit positioned such that at least a portion of said concentration unit is constructed within, adhered to or contiguous with a first substrate, said concentration unit comprising:
      at least one first sample microchannel through which a liquid comprising charged species can be made to pass from a first side to a second side, wherein at least a portion of said first channel is exposed to the environment;
      at least one second sample microchannel through which said liquid comprising charged species can be made to pass from a first side to a second side, wherein at least a portion of said second channel is exposed to the environment, the separation between the exposed portions of said first sample microchannel and said second sample microchannel ranges between 50 micrometers and 1000 micrometers;
      at least one buffer microchannel or reservoir comprising a buffer;
      at least one conduit proximal to said sample microchannels and linked to said buffer microchannel or reservoir; and
      at least one unit to induce an electric field in said conduit, said sample microchannel, said buffer microchannel or reservoir or a combination thereof.

2. The concentration device of claim 1, wherein said sample microchannels comprise liquid or solution comprising a charged species of interest and wherein said concentration unit comprises a droplet of said liquid or solution, said droplet at least partially exposed to the environment, wherein said droplet is in contact with said sample microchannels and said conduit.

3. The concentration unit of claim 1, wherein at least a portion of said concentration unit is positioned proximally to or adhered to a plate, wherein said plate supports, seals and/or stabilizes at least a portion of said concentration unit and wherein said plate is in contact with said droplet.

4. The device of claim 1, wherein the width and/or depth of said sample microchannels, said at least one buffer microchannel or reservoir or a combination thereof is between 0.5-100 μm.

5. The device of claim 1, wherein said conduit is a nanochannel and/or wherein said conduit comprising a polymer-based permselective material comprising a cation selective or an anion selective material or wherein said conduit comprising a nanoporous structure made from closed-packed microbeads or nanobeads, which may or may not be coated with a cation selective or an anion selective material.

6. The device of claim 2, wherein said droplet diameter or droplet longest dimension ranges between 400 micrometers and 1000 micrometers and wherein said droplet shape is spherical, hemispherical, or of any other contour shape.

7. The device of claim 1, wherein said device is comprised of a transparent material wherein said transparent material is borosilicate glass, silicon dioxide, polydimethylsiloxane (PDMS), silicon nitride, quartz or SU-8.

8. The concentration device of claim 2, comprising an array of concentration units.

9. The array of claim 8, wherein said concentration units are stacked such that the two long axes of each unit are arranged in parallel to the two long axes of a neighboring concentration unit, and such that the region of said microchannels that is exposed to the environment in at least two of said units is directed to the same side with respect to said at least two concentration units or wherein said concentration units are positioned such that the shortest axis and one of the longer axes of said units are arranged in parallel to the shortest axis and one of the longer axes of a neighboring concentration unit, and such that the region of said microchannels that is exposed to the environment in at least two of said units is directed to the same side with respect to said at least two concentration units and wherein said droplets are on the same plane.

10. The array of claim 8, wherein said array is positioned on top of a substrate and/or wherein said array is fixed to said substrate and wherein said droplets are temporarily in contact with said substrate.

11. The array of claim 10, wherein regions on said substrate that are proximal to said droplets are coated with an indicator species, capable of interacting with said charged species and/or wherein said regions on said substrate that are proximal to said droplet are connected to a measurement device, wherein said measurement device optionally measures fluorescence and/or wherein said regions on said substrate that are proximal to said droplet comprises cavities.

12. The array of claim 10, wherein said regions on said substrate that are proximal to said droplets fit a syringe or a dispenser array and wherein said syringe or dispenser array is used to transfer the contents of said regions on said substrate that are proximal to said droplets to an assay system and/or wherein said syringe or dispenser array is used to add assay material to the regions on said substrate that are proximal to said droplets.

13. The concentration device of claim 8, wherein the spacing between rows or columns or combination thereof within said array approximates in width to one or more diameter or one of more longest dimension of a droplet formed by said concentration unit.

14. The array of claim 10, wherein said array further comprising at least one supporting structure positioned between said concentration units, which aids in separating, fixing, stabilizing and keeping a desired distance between said concentration units and/or wherein said array further comprising at least one supporting structure positioned between said concentration units and said substrate, which aids in suspending said concentration units over said substrate, at a desired height.

15. The array of claim 10, wherein said supporting structure comprises a shift mechanism, wherein said shift mechanism comprises a pump, a screw, a gear, shaft, a flexible, pressed or elastic material, a wheel, a lever, a magnet, a coil, micromanipulators or a combination thereof and wherein said shift mechanism is mechanical, pneumatic, electrical, magnetic, electrically-controlled, computerized or a combination thereof.

16. The array of claim 8, wherein said array comprises at least 1000 concentration units.

17. The concentration device of claim 1, further comprising controllers to maintain desirable environmental conditions, wherein said environmental conditions comprises pressure, temperature, pH, CO2 or Oxygen conditions, or a combination thereof.

18. A method for concentrating a species of interest in a liquid, said method comprising the steps of:
   introducing a liquid comprising charged species from a source into a microfluidic electrokinetic concentration device comprising:
      at least one concentration unit positioned such that at least a portion of said concentration unit is constructed within, adhered to or contiguous with a first substrate, said concentration unit comprising:
- at least one first sample microchannel through which a liquid comprising charged species can be made to pass from a first side to a second side, wherein at least a portion of said first channel is exposed to the environment;
- at least one second sample microchannel through which said liquid comprising charged species can be made to pass from a first side to a second side, wherein at least a portion of said second channel is exposed to the environment;
- at least one buffer microchannel or reservoir comprising a buffer;
- at least one conduit proximal to said sample microchannels and linked to said buffer microchannel or reservoir; and
- at least one unit to induce an electric field in said conduit, said sample microchannel, said buffer microchannel or reservoir or a combination thereof;

Such that a droplet of liquid, at least partially exposed to the environment, is brought into contact with said first sample microchannel, said second sample microchannel, and said conduit;
- inducing a first electric field in said sample microchannels and in said droplet whereby electroosmotic flow is induced in said sample microchannels, said flow further introducing said liquid into said device through said sample microchannels and said flow is controlled by the strength of said first electric field; and
- inducing a second electric field in said conduit, whereby charged species depletion occurs in a region proximal to said conduit within said droplet and whereby said charged species are confined to another region within said droplet.

19. The method of claim 18, wherein said liquid introduction from a source into said microfluidic device comprising the use of a pressure inducing unit, an electroosmotic flow inducing unit or a combination thereof.

20. The method of claim 19, wherein said pressure inducing unit, said electroosmotic flow inducing unit or a combination thereof control the size of said droplet.

21. The method of claim 18, wherein at least a portion of said concentration unit further comprises a second substrate positioned proximally to or adhered to said first substrate or a portion thereof, wherein said second substrate supports, seals and/or stabilizes at least a portion of said concentration unit and wherein said second substrate is in contact with said droplet.

22. The method of claim 18, wherein said first electric field in said sample microchannels and in said droplet is generated by applying a higher voltage to said first sample microchannel and a lower voltage to said second sample microchannel.

23. The method of claim 22, wherein said higher voltage, said lower voltage or a combination thereof is positive voltage and wherein said positive voltage is between 50 mV and 500 V.

24. The method of claim 22, wherein said higher voltage is positive and said lower voltage is achieved by electrically grounding said second sample microchannel.

25. The method of claim 22, wherein said second electric field in said conduit is generated by applying a higher voltage to the side of said conduit that is linked to said droplet and a lower voltage to the side of said conduit that is linked to said buffer microchannel and wherein said higher voltage is positive and said lower voltage is applied by electrically grounding said buffer microchannel or reservoir linked to said conduit.

26. The method of claim 25, wherein said higher voltage is the result of said two voltages applied to said first and to said second sample microchannels and wherein said higher voltage has an intermediate value lying between the values of said two voltages applied to said first and to said second sample microchannels.

27. The method of claim 18, wherein said first and second electric fields are induced by applying a voltage of 400 V to said first sample microchannel and by applying a voltage of 350 V to said second sample microchannel and wherein said buffer microchannel or reservoir is electrically grounded.

28. The device of claim 18, wherein droplet diameter or droplet longest dimension ranges between 400 micrometers and 1000 micrometers and wherein said droplet shape is spherical, hemispherical, or any other contour shaped.

29. The method of claim 18, wherein the separation between the exposed portions of said first sample microchannel and said second sample microchannel ranges between 50 micrometers and 1000 micrometers.

30. The method of claim 18, wherein said conduit is a nanochannel and/or wherein said conduit comprising a polymer-based permselective material, wherein said polymer-based permselective material comprising a cation selective or an anion selective material or wherein said conduit comprising a nanoporous structure made from closed-packed microbeads or nanobeads, which may or may not be coated with a cation selective or an anion selective material.

31. The method of claim 18, wherein said device is comprised of a transparent material, wherein said transparent material comprises borosilicate glass, silicon dioxide, polydimethylsiloxane (PDMS), silicon nitride, quartz or SU-8.

32. The method of claim 18, wherein liquid flow speed in said sample microchannel is between 100 μm/sec and 10 mm/sec and wherein liquid volume flow rate is at least 1 L/min.

33. The method of claim 18, wherein said concentration device comprising an array of concentration units.

34. The method of claim 33, wherein said concentration units are stacked such that the two long axes of each unit are arranged in parallel to the two long axes of a neighboring concentration unit, and such that the region of said microchannels that is exposed to the environment in at least two of said units is directed to the same side with respect to said at least two concentration units or wherein said concentration units are positioned such that the shortest axis and one of the longer axes of said units are arranged in parallel to the shortest axis and one of the longer axes of a neighboring concentration unit, and such that the region of said microchannels that is exposed to the environment in at least two of said units is directed to the same side with respect to said at least two concentration units and wherein said droplets are on the same plane.

35. The method of claim 33, wherein said array is positioned on top of a substrate and/or wherein said array is fixed to said substrate and/or wherein said droplets are temporarily in contact with said substrate.

36. The method of claim 35, wherein regions on said substrate that are proximal to said droplets are coated with an indicator species, capable of interacting with said charged species and wherein said indicator species reacts with said concentrated charged species contained in said droplet and wherein said reaction results in identification, quantification or a combination thereof of said concentrated charged species.

37. The method of claim 35, wherein said regions on said substrate that are proximal to said droplet are connected to a measurement device, wherein said measurement device optionally measures fluorescence.

38. The method of claim 35, wherein said regions on said substrate that are proximal to said droplet comprises cavities.

39. The method of claim 35, wherein said regions on said substrate that are proximal to said droplets fit a syringe or a dispenser array and wherein said syringe or dispenser array is used to transfer the contents of said regions on said substrate that are proximal to said droplets to an assay system and/or wherein said syringe or dispenser array is used to add assay material to the regions on said substrate that are proximal to said droplets.

40. The method of claim 33, wherein the spacing between rows or columns or combination thereof within said array approximates in width to one or more diameter or longest dimension of a droplet formed by said concentration unit.

41. The method of claim 33, wherein said array further comprising at least one supporting structure positioned between said concentration units, which aids in separating, fixing, stabilizing and keeping a desired distance between said concentration units or wherein said array further comprising at least one supporting structure positioned between said concentration units and said substrate, which aids in suspending said concentration units over said substrate at a desired height and in bringing said concentration units in contact with said substrate and wherein said supporting structure is used to transfer at least a portion of said droplet from said concentration unit to said substrate.

42. The method of claim 33, wherein said supporting structure comprises a shift mechanism, said shift mechanism comprises a pump, a screw, a gear, shaft, a flexible, pressed and/or elastic material, a wheel, a lever, a magnet, a coil, micromanipulators or a combination thereof and wherein said shift mechanism is mechanical, pneumatic, electrical, magnetic, electrically-controlled, computerized or a combination thereof.

43. The method of claim 33, wherein said array comprises at least 1000 concentration units.

44. The method of claim 18, wherein at least a portion of said droplet comprising the confined charged species is transferred to a substrate, a vessel, a tip, a syringe, a container, a test-tube, an absorbing material, a filter paper, a column or a TLC plate and wherein said transfer is performed by bringing said droplet into contact with said substrate, vessel, tip, syringe, container, test-tube, absorbing material, filter paper, column or TLC plate; and by retrieving said substrate, vessel, tip, syringe, container, test-tube, absorbing material, filter paper, column or TLC plate.

45. The method of claim 18, wherein said concentration device further comprising controllers to maintain desirable environmental conditions, wherein said environmental conditions comprising pressure, temperature, pH, CO2 or Oxygen conditions, or a combination thereof.

* * * * *